(12) United States Patent
Enoki et al.

(10) Patent No.: US 6,608,032 B1
(45) Date of Patent: *Aug. 19, 2003

(54) MEDICINAL COMPOSITIONS

(75) Inventors: Tatsuji Enoki, Otsu (JP); Hiroaki Sagawa, Kusatsu (JP); Jun Tomono, Muko (JP); Takanari Tominaga, Otsu (JP); Eiji Nishiyama, Moriyama (JP); Hua-Kang Wu, Otsu (JP); Ikunoshin Kato, Uji (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/889,732

(22) PCT Filed: Jan. 18, 2000

(86) PCT No.: PCT/JP00/00184

§ 371 (c)(1),
(2), (4) Date: Sep. 4, 2001

(87) PCT Pub. No.: WO00/43018

PCT Pub. Date: Jul. 27, 2000

(30) Foreign Application Priority Data

Jan. 20, 1999 (JP) ............................. 11/011646
Jul. 6, 1999 (JP) ............................. 11/191808
Sep. 24, 1999 (JP) ............................. 11-270285

(51) Int. Cl.⁷ ............................................. A01N 43/04
(52) U.S. Cl. ........................... 514/23; 514/25; 536/4.1; 424/439
(58) Field of Search ...................... 514/23, 25; 424/439; 536/4.1

(56) References Cited

U.S. PATENT DOCUMENTS 6,475,990 B1 * 11/2002 Enoki et al. ................. 514/23

* cited by examiner

Primary Examiner—James O. Wilson
Assistant Examiner—Ganapathy Krishnan
(74) Attorney, Agent, or Firm—Browdy and Neimark PLLC

(57) ABSTRACT

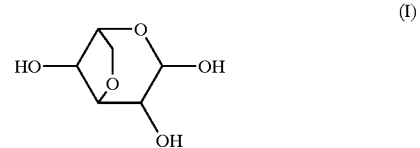

Medicinal compositions for treating or preventing diabetes, rheumatoid, diseases wherein inflammation should be inhibited, diseases wherein α-glycosidase should be inhibited, diseases wherein the synthesis of prostaglandin should be inhibited, diseases wherein endotoxin shock should be inhibited, diseases wherein the production of interleukin should be inhibited, diseases wherein the production of heme oxygenase should be induced, and diseases wherein the production of tumor necrosis factor or carcinogenesis should be inhibited, which contain as the active ingredient at least one compound selected from the group consisting of 3,6-anhydrogalactopyranose represented by formula (I), its aldehyde, its hydrate and 2-O-methylated derivatives and 2-O-sulfated derivatives thereof.

9 Claims, 18 Drawing Sheets

MEDICINAL COMPOSITIONS

The present application is the national stage under 35 U.S.C. §371 of international application PCT/JP00/00184, filed Jan. 18, 2000 which designated the United States, and which application was not published in the English language.

TECHNICAL FIELD

The present invention relates to a pharmaceutical composition. More specifically, the present invention relates to a pharmaceutical composition containing a physiologically active substance derived from algae as an active ingredient. The present invention also relates to a functional food or a functional drink containing the physiologically active composition.

BACKGROUND ART

It is considered that inflammation results from protective action of a living body against invasion from outside, which action causes production of endogenous active substances to allow the physical condition to adapt. However, in many cases, the response caused by the above-mentioned events often becomes harmful and causes disease states. Inflammation associated with an autoimmune disease results from recognition of autologous cells as foreign substances by immune cells, which results in damaging of normal cells.

Rheumatoid arthritis, one of autoimmune diseases, is inflammation specific to joints. As pharmacotherapies for rheumatoid arthritis, internal therapies using steroidal or non-steroidal anti-inflammatory drugs and remission-introducing drugs (gold, D-penicillamine, etc.) are conducted.

Oligosaccharides derived from algae such as agar are expected to be developed as raw materials for foods (Food Chemical, 1988-2, 40–44; Bessatsu Food Chemical (Extra Number Food Chemical)-4, 1990, December, 127–131; JP-A 6-38691). However, their anti-inflammatory or anti-rheumatic activity is unknown.

OBJECTS OF INVENTION

The main object of the present invention is to develop a highly safe substance having physiological functions such as an anti-inflammatory activity and an antirheumatic activity, as well as to provide a pharmaceutical composition for a disease sensitive to the compound (an anti-inflammatory composition, an antirheumatic composition, etc.) containing the substance as an active ingredient, a functional food or a functional drink containing the substance as a constituent component, and the like.

SUMMARY OF INVENTION

The present invention is outlined as follows. The first aspect of the present invention relates to a pharmaceutical composition which contains as an active ingredient at least one member selected from the group consisting of:

a compound selected from the group consisting of 3,6-anhydrogalactopyranose of formula I:

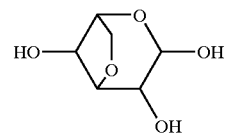

(I)

an aldehyde and a hydrate thereof, and 2-O-methylated derivatives and 2-O-sulfated derivatives of the 3,6-anhydrogalactopyranose, the aldehyde and the hydrate; and a soluble saccharide containing said compound at its reducing end, said pharmaceutical composition being used for treating or preventing diabetes, rheumatism, a disease that requires inhibition of inflammation for its treatment or prevention, a disease that requires inhibition of α-glycosidase for its treatment or prevention, a disease that requires inhibition of prostaglandin synthesis for its treatment or prevention, a disease that requires inhibition of endotoxin shock for its treatment or prevention, a disease that requires inhibition of interleukin production for its treatment or prevention, a disease that requires induction of heme oxygenase production for its treatment or prevention, a disease that requires inhibition of tumor necrosis factor production for its treatment or prevention, or a disease that requires inhibition of carcinogenesis for its treatment or prevention.

The second aspect of the present invention relates to a food or a drink which contains, which is produced by adding thereto, and/or which is produced by diluting at least one member selected from the group consisting of:

a compound selected from the group consisting of 3,6-anhydrogalactopyranose of formula I, an aldehyde and a hydrate thereof, and 2-O-methylated derivatives and 2-O-sulfated derivatives of the 3,6-anhydrogalactopyranose, the aldehyde and the hydrate; and a soluble saccharide containing said compound at its reducing end, said food or drink being used for ameliorating the disease states of or preventing diabetes, rheumatism, a disease that requires inhibition of inflammation for its treatment or prevention, a disease that requires inhibition of α-glycosidase for its treatment or prevention, a disease that requires inhibition of prostaglandin synthesis for its treatment or prevention, a disease that requires inhibition of endotoxin shock for its treatment or prevention, a disease that requires inhibition of interleukin production for its treatment or prevention, a disease that requires induction of heme oxygenase production for its treatment or prevention, a disease that requires inhibition of tumor necrosis factor production for its treatment or prevention, or a disease that requires inhibition of carcinogenesis for its treatment or prevention.

The third aspect of the present invention relates to use of at least one member selected from the group consisting of:

a compound selected from the group consisting of 3,6-anhydrogalactopyranose of formula I, an aldehyde and a hydrate thereof, and 2-O-methylated derivatives and 2-O-sulfated derivatives of the 3,6-anhydrogalactopyranose, the aldehyde and the hydrate; and a soluble saccharide containing said compound, for the manufacture of an antidiabetic composition, an anti-rheumatic composition, an anti-inflammatory composition, a composition for inhibiting α-glycosidase, a composition for inhibiting prostaglandin synthesis, a composition for inhibiting endotoxin shock, a composition for inhibiting interleukin production, a composition for inducing heme oxygenase production, a composition for inhibiting tumor necrosis factor production or a composition for inhibiting carcinogenesis.

DETAILED DESCRIPTION OF THE INVENTION

Figure 1:
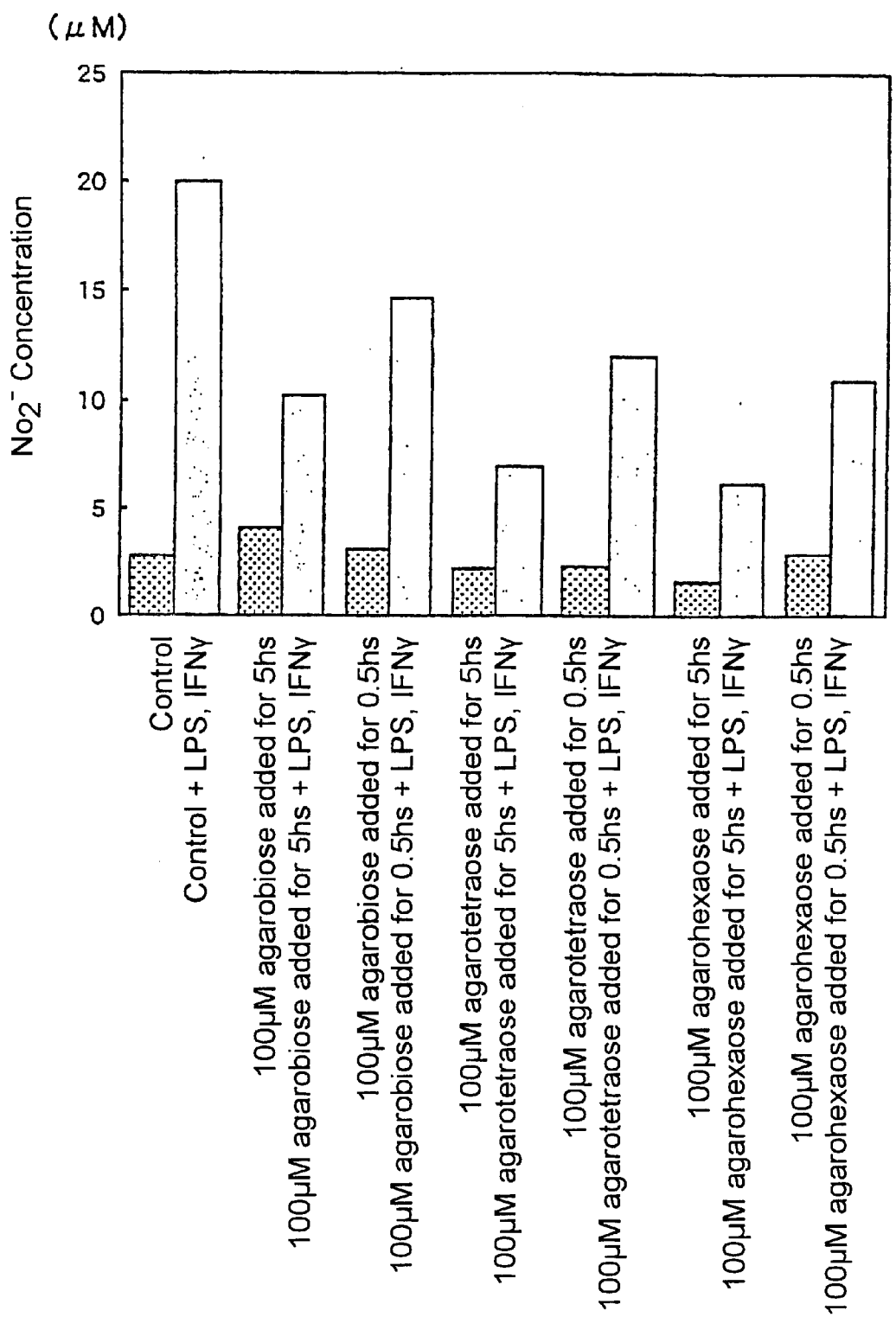
FIG. 1 illustrates the $NO_2^{31}$ concentration in a culture medium obtained by culturing under various culture conditions with the addition of agarobiose, agarotetraose or agarohexaose.

An aldehyde of 3,6-anhydrogalactopyranose of formula I (hereinafter simply referred to as 3,6-anhydrogalactopyranose) of the present invention is a compound of formula II below. A hydrate of the 3,6-anhydrogalactopyranose is a compound of formula III below. A 2-O-methylated derivative and a 2-O-sulfated derivative of the 3,6-anhydrogalactopyranose are a compound of formula IV below and a compound of formula V below, respectively. An aldehyde of the 2-O-methylated derivative and an aldehyde of the 2-O-sulfated derivative are a compound of formula VI below and a compound of formula VII below, respectively. A hydrate of the 2-O-methylated derivative and a hydrate of the 2-O-sulfated derivative are a compound of formula VIII below and a compound of formula IX below, respectively.

Formula II:

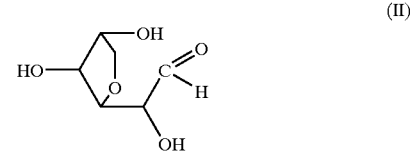

(II)

Formula III:

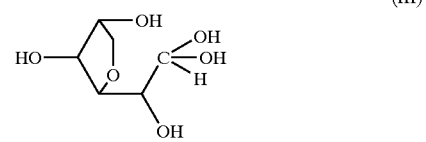

(III)

Formula IV:

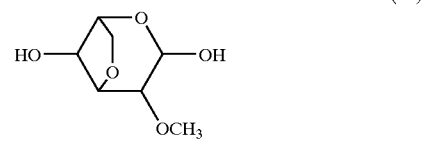

(IV)

Formula V:

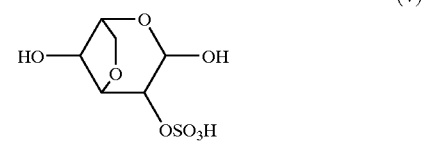

(V)

Formula VI:

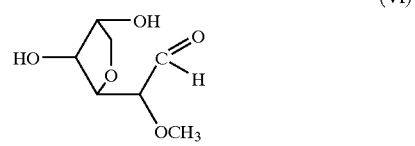

(VI)

Formula VII:

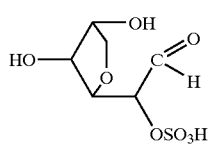

(VII)

Formula VIII:

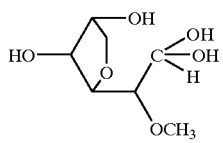

(VIII)

Formula IX:

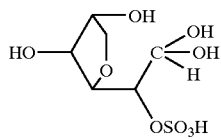

(IX)

The structures of formulas I to IX used herein may be represented by different expression forms. It is intended that such different expression forms and their possible tautomers are included in formulas I to IX. In addition, the configuration of formulas I to IX is not limited to specific one as long as the desired activities are exerted, and may be in the D-form or L-form, or a mixture thereof.

The soluble saccharide of the present invention is, without limitation, a soluble saccharide containing at least one compound selected from the group consisting of 3,6-anhydrogalactopyranose, an aldehyde and a hydrate thereof, and 2-O-methylated derivatives and 2-O-sulfated derivatives of the 3,6-anhydrogalactopyranose, the aldehyde and the hydrate (hereinafter collectively referred to as "the compounds of formulas I to IXI"). The soluble saccharide of the present invention can be obtained by decomposition of a substance containing at least one compound selected from the compounds of formulas I to IX (hereinafter simply referred to as a raw substance) under acidic conditions below pH 7 with an acid and/or by digestion of the raw substance with an enzyme, or by chemical synthesis. The soluble saccharide of the present invention is not limited to any specific one as long as it does not solidify or semi-solidify (gelate) when used. Therefore, any saccharides containing at least one compound selected from the compounds of formulas I to IX which become solated when used are included in the soluble saccharides of the present invention. The soluble saccharides suitably used in the present invention are exemplified by a saccharide whose non-reducing end is a sugar other than L-galactose-6-sulfate and include, for example, saccharides such as agarobiose, agarotetraose, agarohexaose, agarooctaose, κ-carabiose and β-galactopyranosyl-3,6-anhydro-2-O-methyl-L-galactose.

The raw substances used for obtaining the soluble saccharides are not limited to any specific one and are exemplified by viscous polysaccharides from red algae such as agarose, agaropectin, funoran, porphyran, carrageenan, furcellaran, and hypnean [Kyoritsu-shuppan Inc., "Tatouseikagaku 1—Kagakuhen—(Biochemistry of Polysaccharides 1—Chemistry), pp. 314 (1969)]. The raw substances also include materials that contain these polysaccharides. For example, as raw materials for agarose and agaropectin, red algae belonging to Gelidiaceae such as *Gelidium amansil*, *Gelidium japonicum*, *Gelidium pacificum*, *Gelidium subcostatum*, *Pterocladia tenuis* and *Acanthopeltis japonica*, red algae belonging to Gracilariaceae such as *Gracilaria verrucosa* and *Gracilaria gigas*, red algae belonging to Ceramiaceae such as *Ceramium kondoi* and *Campylaephora hypnaeoides*, and other red algae are used. Usually, several kinds of algae are used in combination as the raw materials. Although algae dried in the sun are usually used as the raw materials, both fresh and dried algae can be used in the present invention. Algae which are bleached while being sprayed with water during drying, i.e., bleached raw algae, can also be used.

The raw material algae are extracted with hot water and then cooled to obtain "gelidium jelly". Agar is obtained by removing water from the "gelidium jelly" by freeze-dehydration or compress-dehydration, and then drying it. Agar in various forms such as bar, belt, board, thread and powder can be used regardless of the source algae. Usually, agar contains about 70% of agarose and about 30% of agaropectin. The agar can be further purified to prepare agarose with high purity. Purified agarose with high purity or low purity having various agarose contents can be used.

The raw substances include the above-mentioned raw material algae for agar, gelidium jelly, agar, purified agarose and purified agaropectin as well as intermediate products and side products obtained during preparation of these substances.

Agarose is a polysaccharide that has a principal structure in which D-galactose and 3,6-anhydro-L-galactose are alternately linked each other. In the structure, the 1-position of D-galactose is linked to the 4-position of 3,6-anhydro-L-galactose through a β-glycoside bond, and the 1-position of 3,6-anhydro-L-galactose is linked to the 3-position of D-galactose through an α-glycoside bond. The α-1,3-bond is hydrolyzed by mild hydrolysis with a dilute acid or α-agarase [Carbohydr. Res., 66: 207 (1978)]. The β-1,4-bond is selectively hydrolyzed by β-agarase.

Carrageenan is a polysaccharide which is contained in red algae such as Gigartinaceae, Solieriaceae and Hypneaceae. κ-Carrageenan, λ-carrageenan and η-carrageenan are known.

κ-Carrageenan has a fundamental structure in which the 1-position of D-galactose-4-sulfate is linked to the 4-position of 3,6-anhydro-D-galactose through a β-glycoside bond, the 1-position of 3,6-anhydro-D-galactose is linked to the 3-position of D-galactose-4-sulfate through an α-glycoside bond, and they are repeated alternately. λ-Carrageenan has a fundamental structure in which the 1-position of D-galactose is linked to the 4-position of D-galactose-2,6-disulfate through a β-glycoside bond, the 1-position of D-galactose-2,6-disulfate is linked to the 3-position of D-galactose through an α-glycoside bond, and they are repeated alternately. Carrageenan is utilized as a gelling agent for foods.

The raw substances of the present invention also include partially decomposed products of the above-mentioned raw substances obtained by using a chemical, physical and/or enzymatic method.

Examples of chemical decomposition methods include hydrolysis under acidic to neutral conditions. Examples of physical decomposition methods include radiation of electromagnetic waves or ultrasonic waves. Examples of enzymatic digestion methods include hydrolysis with a hydrolase such as agarase and carrageenase.

The acidic to neutral conditions used for the decomposition of the raw substances are not limited to specific ones as long as the decomposition produces one of the compounds of formulas I to IX or soluble saccharides each containing at least one of these compounds. The compound or the soluble saccharide has an antidiabetic activity, an antirheumatic activity, an anti-inflammatory activity, an activity of inhibiting α-glycosidase, an activity of inhibiting prostaglandin synthesis, an activity of inhibiting endotoxin shock, an activity of inhibiting interleukin production, an activity of inducing heme oxygenase production, an activity of inhibiting tumor necrosis factor production and/or an activity of inhibiting carcinogenesis. Examples of the saccharides include agarobiose, agarotetraose, agarohexaose, agarooctaose, κ-carabiose (hereinafter simply referred to carabiose) and β-D-galactopyranosyl-3,6-anhydro-2-O-methyl-L-galactose; as well as a saccharide which contains a compound selected from the compounds of formulas I to IX at its reducing end, and whose non-reducing end is a saccharide other than L-galactose-6-sulfate.

For example, the compound selected from the compounds of formulas I to IX or the soluble saccharide containing at least one of these compounds used in the present invention is produce by dissolving or suspending, and reacting a raw substance in an acid. The reaction time required for the production of the compound selected from the compounds of formulas I to IX or the soluble saccharide containing at least one of these compounds is shortened by heating upon reaction.

The type of the acid used for dissolving or suspending the raw substance (e.g., agarose or a substance that contains agarose) is not limited to a specific one. Examples of acids which can be used include inorganic acids such as hydrochloric acid, sulphuric acid and nitric acid, organic acids such as citric acid, formic acid, acetic acid, lactic acid and ascorbic acid, as well as solid acids such as cation exchange resins, cation exchange fibers and cation exchange membranes.

Although the concentration of the acid is not specifically limited, the acid can be used at a concentration of 0.0001 to 5 N, preferably 0.001 to 1 N. In addition, although the reaction temperature is not specifically limited, the reaction may be carried out at 0 to 200° C., preferably 20 to 130° C. Furthermore, although the reaction time is not specifically limited, the reaction may be carried out for a few seconds to a few days. The type and the concentration of the acid, the reaction temperature and the reaction time may be suitable selected depending on the particular kind of the raw substance containing at least one compound selected from the compounds of formulas I to IX (e.g., agarose, carrageenan, etc.), as well as the compound of interest selected from the compounds of formulas I to IX, the yield of the saccharide containing the compound, and the degree of polymerization of the soluble saccharide of interest containing the compound selected from the compounds of formulas I to IX at its reducing end. In general, the acid decomposition reaction proceeds more rapidly by selecting a strong acid rather than a weak acid, a high acid concentration rather than a low acid concentration, and a high temperature rather than a low temperature.

Furthermore, when a solid acid is used, a strong cationic exchange resin generally gives better decomposition reaction efficiency than a weak cationic exchange resin. In addition, the acid decomposition reaction proceeds more rapidly by using a more amount of the solid acid relative to the amount of raw substance and a higher reaction temperature.

For example, a solution of the saccharide used in the present invention which is obtained by suspending agar in 0.1 N hydrochloric acid at a concentration of 10% by weight, dissolving the agar by heating at 100° C. for 13 minutes and removing insoluble materials does not gelate any longer even if the solution is cooled to its freezing point. When saccharides contained in this solution are analyzed by gel filtration HPLC, normal phase HPLC and the like, saccharides with high molecular weight are scarcely observed, and most of the saccharides are decomposed into soluble saccharides composed of 10 or less sugars. Likewise, in case of a solid acid, a solution of the saccharide of the present invention obtained by converting 1 part by weight of Na-type of a commercially available strong cationic exchange resin into H type thereof using 1 N hydrochloric acid, placing it in 79 parts by weight of deionized water, adding and suspending 10 parts by weight of agar, and heating the mixture at 95° C. for 180 minutes dose not gelate any longer even if the solution is cooled to its freezing point. When saccharides contained in this solution are analyzed by gel filtration HPLC, normal phase HPLC and the like, saccharides with high molecular weight are scarcely observed, and most of the saccharides are decomposed into soluble saccharides composed of 10 or less sugars.

Furthermore, for producing a soluble saccharide used in the present invention which contains a compound selected from the compounds of formulas I to IX at its reducing end, an organic acid (e.g., citric acid, lactic acid or malic acid) is used, and the acid concentration (ranging from several 10 mM to several M), the heating temperature (ranging from 70 to 95° C.) and the heating time (ranging from several tens of minutes to 24 hours) are suitably selected, thereby a large amount of the physiologically active oligosaccharide (e.g., a saccharide for an antioxidant) can be produced. In addition, the produced physiologically active oligosaccharide has long-term storage stability if it is maintained under acidic conditions while preventing them from becoming alkaline after hydrolysis.

A decomposition product of a raw substance may be used directly or after neutralizing it as a compound selected from the compounds of formulas I to IX, or a soluble saccharides containing at least one of these compounds used in the present invention, for example, a saccharide such as agarobiose, agarotetraose, agarohexaose, agarooctaose, κ-carabiose or β-D-galactopyranosyl-3,6-anhydro-2-O-methyl-L-galactose. It may be used after further purifying it. A compound selected from the compounds of formulas I to IX, or a soluble saccharide containing the compound at its reducing end (e.g., an oligosaccharide such as agarobiose, agarotetraose, agarohexaose, agarooctaose, κ-carabiose or β-D-galactopyranosyl-3,6-anhydro-2-O-methyl-L-galactose) can be purified by using, for example, its apoptosis-inducing activity or its carcinostatic activity as an index. A known method such as a chemical method or a physical method can be used for purification. A compound selected from the compounds of formulas I to IX or a soluble saccharide containing at least one of the compounds, which is the apoptosis-inducing substance of interest, produced in the acid decomposition process, can be purified by combining known purification methods such as gel filtration, fractionation using a molecular weight fractionating membrane, solvent extraction and various chromatographies using ion exchange resins or the like.

The structures of the resultant compounds can be analyzed by known methods such as mass spectrometry, nuclear magnetic resonance and measurement of ultraviolet absorption spectrum or infrared absorption spectrum.

Agarobiose, an example of the active ingredient of the present invention, is a disaccharide in which the 1-position of D-galactose is linked to the 4-position of 3,6-anhydro-L-galactose through a β-glycoside bond. An α-isomer and a β-isomer exist for agarobiose because an anomer carbon is present at the 1-position of 3,6-anhydro-L-galactose. Both of the isomers are included in the agarobiose used in the present invention.

The saccharide containing the compound selected from the compounds of formulas I to IX at its reducing end used as the active ingredient in the present invention is one in which a sugar is bound to a hydroxide group other than that at the 1-position of the compound selected from the compounds of formulas I to IX. The saccharide is not limited to a specific one as long as it has an antidiabetic activity, an antirheumatic activity, an anti-inflammatory activity, an activity of inhibiting α-glycosidase, an activity of inhibiting prostaglandin synthesis, an activity of inhibiting endotoxin shock, an activity of inhibiting interleukin production, an activity of inducing heme oxygenase production, an activity of inhibiting tumor necrosis factor production and/or an activity of inhibiting carcinogenesis. Examples thereof include decomposition products of the raw substances such as products from agarose obtained by decomposition with acid or digestion with α-agarase, including agarobiose, agarotetraose, agarohexaose, agarooctaose, agarodecaose and β-D-galactopyranosyl-3,6-anhydro-2-O-methyl-L-galactose. Furthermore, products obtained from carrageenan by decomposing it with acid or digesting it with carrageenase, such as carabiose, are exemplified. Furthermore, the saccharides of the present invention which contain compounds selected from the compounds of formulas I to IX at their reducing ends include a saccharide in which one or more sugar selected from the following is bound to a hydroxy group other than that at the 1-position of the compound selected from the compounds of formulas I to IX: hexoses such as glucose, mannose and galactose, pentoses such as xylose, arabinose and ribose, uronic acids such as glucuronic acid, galacturonic acid, mannuronic acid and gluronic acid, amino sugars such as glucosamine and galactosamine, sialic acids such as N-acetylneuraminic acid, and deoxy sugars such as fucose, as well as esters, amides and lactones thereof. Furthermore, the saccharides of the present invention which contain compounds selected from the compounds of formulas I to IX at their reducing ends include a saccharide in which a pyruvate and/or sulfate group is bound to a saccharide containing a compound selected from the compounds of formulas I to IX at its reducing end (e.g., a saccharide such as agarobiose, agarotetraose, agarohexaose, agarooctaose, κ-carabiose or β-D-galactopyranosyl-3,6-anhydro-2-O-methyl-L-galactose), as well as a saccharide whose hydroxy group is methylated. As described above, the saccharide of the present invention which contains a compound selected from the compounds of formulas I to IX at its reducing end is preferably a saccharide whose non-reducing end is a sugar other than L-galactose-6-sulfate.

Since an anomer carbon is present at the 1-position of the compound at the reducing end of the saccharide containing 3,6-anhydrogalactopyranose or its 2-O-methylated derivative at its reducing end, an α-isomer and a β-isomer exist for such a compound. Both of the isomers can be used in the present invention as the saccharide which contains 3,6-anhydrogalactopyranose or its 2-O-methylated derivative at its reducing end.

The molecular weight of the compound is not specifically limited as long as it has a physiological activity such as an antidiabetic activity, an antirheumatic activity, an anti-inflammatory activity, an activity of inhibiting α-glycosidase, an activity of inhibiting prostaglandin synthesis, an activity of inhibiting endotoxin shock, an activity of inhibiting interleukin production, an activity of inducing heme oxygenase production, an activity of inhibiting tumor necrosis factor production and/or an activity of inhibiting carcinogenesis.

Of course, a mixture of an α-isomer, a β-isomer, an aldehyde and a hydrate, and a mixture of a D-isomer and an L-isomer can be used in the present invention as a compound selected from the compounds of formulas I to IX or a compound at the reducing end of the saccharide containing the compound at its reducing end.

A compound selected from the compounds of formulas I to IX or a saccharide containing the compound at its reducing end used in the present invention has an antidiabetic activity, an antirheumatic activity, an anti-inflammatory activity, an activity of inhibiting α-glycosidase, an activity of inhibiting prostaglandin synthesis, an activity of inhibiting endotoxin shock, an activity of inhibiting interleukin production, an activity of inducing heme oxygenase production, an activity of inhibiting tumor necrosis factor production and/or an activity of inhibiting carcinogenesis. The present invention provides a pharmaceutical composition for treating or preventing the following, which composition containing as an active ingredient at least one member selected from the group consisting of a compound selected from the compounds of formulas I to IX, and a soluble saccharide containing the compound at its reducing end: diabetes, rheumatism, a disease that requires inhibition of inflammation for its treatment or prevention, a disease that requires inhibition of α-glycosidase for its treatment or prevention, a disease that requires inhibition of prostaglandin synthesis for its treatment or prevention, a disease that requires inhibition of endotoxin shock for its treatment or prevention, a disease that requires inhibition of interleukin production for its treatment or prevention, a disease that requires induction of heme oxygenase production for its treatment or prevention, a disease that requires inhibition of tumor necrosis factor production for its treatment or prevention, or a disease that requires inhibition of carcinogenesis for its treatment or prevention.

The pharmaceutical composition for treatment or prevention of the present invention can be used as an antidiabetic composition, an antirheumatic composition, an anti-inflammatory composition, a composition for inhibiting α-glycosidase, an anti-hyperglycemic composition, an anti-hyperlipidemic composition, an anti-obese composition, a composition for inhibiting prostaglandin synthesis, a composition for inhibiting endotoxin shock, a composition for inhibiting interleukin production, a composition for inducing heme oxygenase production, a composition for inhibiting tumor necrosis factor production, a composition for inhibiting active oxygen production, a composition for inhibiting nitrogen monoxide (NO) production, a composition for inhibiting peroxide production or a composition for inhibiting carcinogenesis.

Rheumatism is a disease in which synovial cells or chondrocytes are damaged. The compound used in the present invention is useful as an antirheumatic agent based on its antiproliferation activity against synovial cells or the like.

The compound used in the present invention inhibits the production of tumor necrosis factor. It is considered that tumor necrosis factor directly causes inflammation in organ-specific autoimmune diseases (e.g., rheumatoid arthritis) and inflammatory diseases. Thus, it ameliorates disease states of inflammation and rheumatism (in particular, rheumatoid arthritis), resulting in marked decrease in inflammation markers including a C-reactive protein (CRP) value, a rheumatoid factor (RF) value and an erythrocyte sedimentation rate value, as well as remarkable amelioration of complications such as dysbasia.

Tumor necrosis factor was discovered as a factor that induces hemorrhagic necrosis at tumor sites. Tumor necrosis factor is currently recognized as a cytokine that is involved widely in biological defense and immunological mechanism on the basis of inflammation. Failure in the mechanism regulating the production of tumor necrosis factor brings various troubles to the host. Overproduction or unregulated production of tumor necrosis factor is involved in a number of diseases. Such diseases include rheumatoid arthritis, rheumatic myelitis, osteoarthritis, gouty arthritis, sepsis, septic shock, endotoxin shock, Gram-negative bacterial sepsis, toxic shock syndrome, cerebral malaria, chronic pneumonia, graft versus host reaction, allograft rejection, pyrexia and myalgia due to an infectious disease such influenza, cachexia secondary to infection or malignant tumor, cachexia secondary to human acquired immunodeficiency syndrome (AIDS), AIDS, AIDS-related syndrome, keloid formation, ulcerative colitis, multiple sclerosis, and autoimmune diseases such as autoimmune diabetes and systemic lupus erythematosus [Molecular Medicine, 33: 1010–1020, 1182–1189 (1996)].

The composition for inhibiting tumor necrosis factor production of the present invention is useful for treating disease states mediated or worsened by tumor necrosis factor.

The compound used in the present invention is useful for inhibiting the production of oxidizing substances such as active oxygen. Therefore, an antioxidant composition (e.g., a composition for inhibiting active oxygen production) that contains the compound as its active ingredient is useful for treating or preventing diseases caused by production and/or excess of active oxygen.

Examples of diseases that require inhibition of NO production for their treatment or prevention according to the present invention include, but are not limited to, systemic hypotension caused by toxic shock, treatment with certain cytokines and the like, reduction in blood pressure response, autoimmune diseases, inflammation, arthritis, rheumatoid arthritis, diabetes, inflammatory bowel diseases, vascular dysfunction, angiectasis caused by diseases, tissue injury, cardiovascular ischemia, hyperalgesia, cerebral ischemia, diseases accompanying vascularization, and cancers.

NO production is increased during cerebral ischemia and after re-perfusion, resulting in damage to cerebral tissues. Administration of the composition for inhibiting NO production of the present invention to a patient during cerebral ischemia relieves the damage to cerebral tissues and improves the prognosis.

Arachidonic acid metabolism is greatly involved in the rise of inflammation and dolor in tissues. Arachidonic acid derived from phospholipid in cell membrane is metabolized in vivo into three substances, prostaglandin, prostacyclin and thromboxane, by the action of cyclooxygenase. Among these, prostaglandin has an angiectatic activity and, consequently, an activity of increasing blood flow to organs. In particular, prostaglandins $E_2$ and $I_2$ increase edemas and leukocyte infiltration at inflammation sites due to their activity of increasing blood flow. Sedative and anti-inflammatory activities can be exerted by administering the composition for inhibiting prostaglandin $E_2$ synthesis of the present invention to inhibit the biosynthesis of prostaglandin. Furthermore, leukocytes infiltrated into inflammation sites produce active oxygen and cause oxidative stress conditions. Accordingly, the composition for inhibiting prostaglandin $E_2$ synthesis of the present invention which inhibits the biosynthesis of prostaglandin is also useful for the prevention, treatment or prevention of worsening of various diseases caused by oxidative stress as described above.

In addition, NO induces edema which is characteristically observed in inflammatory lesions, i.e., increases vascular permeability, and increases biosynthesis of prostaglandins which are inflammatory mediators as described above. The effect of inhibiting NO production and the effect of inhibiting prostaglandin $E_2$ synthesis of the present invention act synergistically to exhibit sedative and anti-inflammatory activities as well as synergistic effects in the prevention, treatment or prevention of worsening of various diseases caused by oxidative stress.

When 12-O-tetradecanoylphorbol 13-acetate (TPA), a strong tumor promoter, is applied to a skin, arachidonic acid metabolism in cells at the applied site is promoted, resulting in production of chemical substances such as prostaglandin, leukotriene and thromboxane. These inflammatory substances increase vascular permeability and cause edema in the skin. Arachidonic acid metabolites are known to be involved in skin diseases such as acute urticaria including erythema and wheal. It is considered that a substance that inhibits edema caused by TPA is effective for these diseases. A model for a skin disease caused by TPA is used for a model for psoriasis because of the histological similarities. Thus, a substance that inhibits edema caused by TPA is useful as a pharmaceutical composition for treating psoriasis.

The process of carcinogenesis involves a step of mutagenesis in which cellular DNA is damaged (initiation) and a step of deviation of cell growth control (promotion). It is believed that carcinogenesis of cells requires such a process.

DMBA acts as an initiator. TPA acts as a promoter to promote carcinogenesis. Known promotion activities of TPA include a direct mutagenic activity and a carcinogenic activity through induction of inflammation in a living body. Specifically, TPA causes inflammatory cells such as macrophages to release inflammatory mediators such as NO and prostaglandin $E_2$. Prostaglandin $E_2$ selectively activates Th2 cells. The activation of Th2 is involved in suppression of Th1. On the other hand, NO selectively suppresses Th1. Suppression of Th1 by NO or prostaglandin $E_2$ suppresses the protective mechanism of a living body against cancer, resulting in induction of carcinogenesis. Activities of inhibiting carcinogenesis of NSAID, steroid and the like which suppress prostaglandin $E_2$ have been reported.

It has been reported that green tea and catechins contained in green tea have activities of inhibiting carcinogenesis in several literatures (Okabe, S. et al., Jpn. J. Cancer Res. 90: 733–739, 1999; Yamane, T. et al., Molecular Medicine 33: 394–399, 1996; Wang, Z. et al., Cancer Res. 52: 1162–1170, 1992).

Other substances which have been reported to inhibit carcinogenesis include vitamins, non-steroidal anti-inflammatory drugs, minerals such as calcium and selenium, and antioxidants such as N-acetylcysteine. Regarding oligosaccharides, an activity of inhibiting carcinogenesis of lacturose (Ponz de Leon et al., Scand. J. Gastroenterol. Suppl. 222: 72–75, 1997; Challa, A. et al., Carcinogenesis 18: 517–521, 1997), an activity of inhibiting carcinogenesis of colon cancer of galactooligosaccharide (Wijnands, M. V. et al., Carcinogenesis 20: 651–656, 1999) and an activity of inhibiting carcinogenesis of colon cancer and a carcinostatic activity on chest cancer of fructooligosaccharide (or oligofructose) (Pierre, F. et al., Cancer Res. 57: 225–228, 1997; Taper, H. S. et al., J. Nutr. 129: 1488–1491, 1999) have been reported. However, oligosaccharides derived from agar have not been reported to have such activities of inhibiting carcinogenesis.

A member selected from the group consisting of a compound selected from the compounds of formulas I to IX and a soluble saccharide containing the compound at its reducing end suppresses inflammation caused by TPA and suppresses carcinogenesis due to inflammatory agents. Thus, a composition for inhibiting carcinogenesis and a food or a drink for inhibiting carcinogenesis containing a member selected from the above-mentioned compounds as an active ingredient can be manufactured and provided.

Interleukin is a generic name of proteinous biologically active substances produced by lymphocytes, monocytes and the like. Existence of interleukins 1 to 18 is currently known. According to the present invention, interleukins are exemplified by IL-6 and IL-10.

A cDNA for IL-6 was first cloned as one encoding a differentiation factor that induces the terminal differentiation of B cells. IL-6 is involved not only in immune response but also differentiation of cells in hematopoietic system and nerve system as well as acute phase response. It is also closely related to onset of various immunological abnormalities and inflammatory diseases as well as lymphoid tumors. IL-6 induces antibody production in B cells to produce IgM, IgG and IgA classes of immunoglobulins, but is not involved in class switching unlike IL-4. IL-6 acts as a growth factor for B cells and plasmacytes. In addition, it participates with T cells. Specifically, IL-6 allows T cells to grow or differentiate. IL-6 also participates in hematopoietic system. It, in cooperation with IL-3, allows hematopoietic stem cells to grow by shortening G0 phase. It promotes maturation of megakaryocytes to induce increase in platelets. IL-6 is also involved in acute phase response which is an immediate response of a living body to infection with a bacterium or a virus, or malignant tumor. IL-6 also participates with nerve system. It is secreted from cells in nerve system such as glioblastomas and astrocytomas and acts to induce differentiation of nerve system. In case of rheumatoid arthritis and systemic lupus erythematosus, activation of B cells is observed and IL-6 is present in synovial fluid in a patient at a high concentration. In case of Castleman syndrome which is characterized by systemic lymphadenopathy, the concentration of IL-6 in blood is very high. A large amount of IL-6 is produced from tumor cells in a patient with atrial myxoma having autoimmune disease-like symptoms. Furthermore, since the growth of myeloma cells derived from a patient with multiple myeloma is inhibited using an anti-IL-6 antibody, it is highly possible that IL-6 serves as a self growth factor for myeloma cells. IL-6 is contained in urine from a patient with primary glomerulonephritis and acts as a growth factor for renal mesangial cells [Kohei Miyazono and Kazuo Sugamura (eds.), "Bio Science Yogo Library: Cytokine—Growth Factor", pp. 28–29, Yodo-sha (1995)]. It is possible to treat or prevent the conditions of such diseases, which are considered to be caused by abnormal production of IL-6, by administering the compound used in the present invention to inhibit IL-6 production.

Examples of diseases that require inhibition of IL-10 production for their treatment or prevention include a disease that is accompanied by lowered immunity.

Two isozymes of heme oxygenase (HO), HO-1 (33 kDa) and HO-2 (36 kDa), are known. HO-2 has a structure in which an extra amino acid sequence consisting of 20 amino acid residues is added at the N-terminus of HO-1. Although the remaining portions share a homology of 40 to 50%, the high-order structures are very similar each other. Both of them have hydrophobic regions at the C-termini. They are attached to microsome membranes at these portions. Since a soluble fraction having a heme-degrading activity is obtained by treating microsome with trypsin, it is considered that the large domain including the active center protrudes on the cytoplasmic side.

HO-1 is an inducible enzyme. It is remarkably induced in various cells by chemical and physical factors such as heme (the substrate), heavy metal ions, certain organic compounds, hydrogen peroxide, heat shock, UV irradiation and ischemia. HO-2 is a constitutive enzyme. It is expressed in various tissues. In particular, the activity is high in brain and testis. HO degrades heme into biliverdin, CO and iron. Biliverdin is further converted into bilirubin by the action of a reductase. Bilirubin has the following activities as an antioxidant: an antioxidant activity for fatty acid, an activity of scavenging lipid radical, an activity of inhibiting production of hydroperoxides of phospholipids, neutral fat and cholesterol due to oxygen radicals generated in large quantities upon phagocytosis by neutrophils, an activity of inhibiting production of low density lipoprotein (LDL) which is closely related to onset of arteriosclerosis, and an activity of scavenging singlet oxygen. Thus, bilirubin plays an important role in a living body as an endogenous antioxidant. Various radicals act on various biological substances including proteins and nucleic acids in addition to lipids as factors that cause chronic diseases and cancer. Bilirubin reduces the various radicals (Porphyrin Kenkyu-kai (ed.) "Porphyrin/Heme no seimeikagaku: idenbyo, gan, kogaku oyo nado he no tenkai" Tokyo Kagaku Dozin (1995)). Thus, it is possible to induce production of bilirubin, which has an antioxidant activity, by inducing HO to treat or prevent diseases due to various radicals. The compound used in the present invention induces HO production and is useful for treating or preventing diseases that require induction of HO production for their treatment or prevention as described above.

The above-mentioned pharmaceutical composition for treatment or prevention of the present invention (e.g., the antidiabetic composition) can be formulated by using at least one member selected from the group consisting of a compound selected from the compounds of formulas I to IX and a soluble saccharide containing the compound at its reducing end as an active ingredient, and formulating it with a known pharmaceutical carrier.

The compound is generally mixed with a pharmaceutically acceptable liquid or solid carrier and, optionally, solvent, dispersing agent, emulsifier, buffering agent, stabilizer, excipient, binder, disintegrant, lubricant and the like to formulate it. The formulation may be in a form of a solid preparation such as tablet, granule, powder, epipastic and capsule, or a liquid preparation such as normal solution, suspension and emulsion. In addition, it may be formulated into a dried preparation, which can be reconstituted as a liquid preparation by adding an appropriate carrier before use.

The pharmaceutical composition of the present invention can be administrated as either an oral preparation or a parenteral preparation such as injectable preparation and drips.

The pharmaceutical carrier can be selected according to the above-mentioned particular administration route and dosage form. For an oral preparation, starch, lactose, sucrose, mannit, carboxymethylcellulose, cornstarch, inorganic salts and the like are utilized, for example. Binder, disintegrant, surfactant, lubricant, fluidity-promoting agent, tasting agent, coloring agent, flavoring agent and the like can also be included in oral preparations.

A parenteral preparation can be prepared according to conventional methods by dissolving or suspending the saccharide having an activity of inducing apoptosis as an active ingredient of the present invention in a diluent. The diluents include injectable distilled water, physiological saline, aqueous glucose solution, injectable vegetable oil, sesame oil, peanut oil, soybean oil, corn oil, propylene glycol and polyethylene glycol. Optionally, sterilizer, stabilizer, osmotic regulator, smoothing agent and the like may be added to the solution or suspension.

The pharmaceutical composition of the present invention is administered through a suitable route for the dosage form of the composition. The administration route is not limited to a specific one. The pharmaceutical composition can be administered internally or externally (or topically) or by injection. The injectable preparation can be administrated intravenously, intramuscularly, subcutaneously, intradermally and the like, for example. External preparations include a suppository.

A dosage of the pharmaceutical composition of the present invention (e.g., the antidiabetic composition) is appropriately determined and varies depending on the particular dosage form, administration route and purpose as well as age, weight and conditions of a patient to be treated. In general, a daily dosage for an adult person is 10 $\mu$g to 200 mg/kg in terms of the amount of the active ingredient contained in the formulation. Of course, the dosage can vary depending on various factors. Therefore, in some cases, a less dosage than the above may be sufficient but, in other cases, a dosage more than the above may be required. The pharmaceutical composition of the present invention can be administrated orally as it is, or it can be taken daily by adding to selected foods and drinks.

Similarly, the antirheumatic composition, the anti-inflammatory composition, the composition for inhibiting $\alpha$-glycosidase, the anti-hyperglycemic composition, the anti-hyperlipidemic composition, the anti-obese composition, the composition for inhibiting prostaglandin synthesis, the composition for inhibiting endotoxin shock, the composition for inhibiting interleukin production, the composition for inducing heme oxygenase production, the composition for inhibiting tumor necrosis factor production or the composition for inhibiting carcinogenesis of the present invention can be formulated by using at least one member selected from the group consisting of a compound selected from the compounds of formulas I to IX and a soluble saccharide containing the compound at its reducing end as an active ingredient, and formulating it with a known pharmaceutical carrier. These compositions can be produced according to the same manner as that as described above with respect to the production of the pharmaceutical composition.

The antirheumatic composition, the anti-inflammatory composition, the composition for inhibiting $\alpha$-glycosidase, the anti-hyperglycemic composition, the anti-hyperlipidemic composition, the anti-obese composition, the composition for inhibiting prostaglandin synthesis, the composition for inhibiting endotoxin shock, the composition for inhibiting interleukin production, the composition for inducing heme oxygenase production, the composition for inhibiting tumor necrosis factor production or the composition for inhibiting carcinogenesis is administered through a suitable route for the dosage form of the composition. The administration route is not limited to a specific one. The composition can be administered internally or externally (or topically) or by injection. The injectable preparation can be administrated intravenously, intramuscularly, subcutaneously, intradermally and the like, for example. External preparations include a suppository.

A dosage of the antirheumatic composition, the anti-inflammatory composition, the composition for inhibiting $\alpha$-glycosidase, the anti-hyperglycemic composition, the anti-hyperlipidemic composition, the anti-obese composition, the composition for inhibiting prostaglandin synthesis, the composition for inhibiting endotoxin shock, the composition for inhibiting interleukin production, the composition for inducing heme oxygenase production, the composition for inhibiting tumor necrosis factor production or the composition for inhibiting carcinogenesis is appropriately determined and varies depending on the particular dosage form, administration route and purpose as well as age, weight and conditions of a patient to be treated. In general, a daily dosage for an adult person is 10 $\mu$g to 200 mg/kg in terms of the amount of the active ingredient contained in the formulation. Of course, the dosage can vary depending on various factors. Therefore, in some cases, a less dosage than the above may be sufficient but, in other cases, a dosage more than the above may be required. The pharmaceutical composition of the present invention can be administrated orally as it is, or it can be taken daily by adding to selected foods and drinks.

The food or drink of the present invention is that containing, produced by adding thereto and/or produced by diluting at least one member selected from the group consisting of a compound selected from the compounds of formulas I to IX and a soluble saccharide containing the compound, for example, a saccharide prepared by acid decomposition under acidic conditions below pH 7 and/or enzymatic digestion of a raw substance (e.g., agarobiose, agarotetraose, agarohexaose, agarooctaose, $\kappa$-carabiose or $\beta$-D-galactopyranosyl-3,6-anhydro-2-O-methyl-L-galactose). The food or drink has an antidiabetic activity, an antirheumatic activity, anti-inflammatory activity, an activity of inhibiting $\alpha$-glycosidase, an anti-hyperglycemic activity, an anti-hyperlipidemic activity, an anti-obese activity, an activity of inhibiting prostaglandin synthesis, an activity of inhibiting endotoxin shock, an activity of inhibiting interleukin production, an activity of inducing heme oxygenase production, an activity of inhibiting tumor necrosis factor production and/or an activity of inhibiting carcinogenesis. Therefore, it is very useful for ameliorating disease states of and preventing diseases sensitive to at least one member selected from the group consisting of a compound selected from the compounds of formulas I to IX and a soluble saccharide containing the compound. Such diseases include diabetes, rheumatism, a disease that requires inhibition of inflammation for its treatment or prevention, a disease that requires inhibition of $\alpha$-glycosidase for its treatment or prevention, a disease that requires inhibition of prostaglandin synthesis for its treatment or prevention, a disease that requires inhibition of endotoxin shock for its treatment or prevention, a disease that requires inhibition of interleukin production for its treatment or prevention, a disease that requires induction of heme oxygenase production for its treatment or prevention, or a disease that requires inhibition of tumor necrosis factor production for its treatment or prevention. Furthermore, it is useful for inhibition of carcinogenesis.

The process for producing the food or drink of the present invention is not limited to a specific one. Any processes including cooking, processing and other generally employed processes for producing foods and drinks can be used as long as the resultant food or drink contains as its active ingredient at least one member selected from the group consisting of a compound selected from the compounds of formulas I to IX and a soluble saccharide containing the compound at its reducing end, for example, a saccharide prepared by acid decomposition under acidic conditions below pH 7 and/or enzymatic digestion of a raw substance (e.g., agarobiose, agarotetraose, agarohexaose, agarooctaose, κ-carabiose and β-D-galactopyranosyl-3,6-anhydro-2-O-methyl-L-galactose).

The food or drink of the present invention is not limited to a specific one and examples thereof include the following: products of processed cereal (e.g., wheat flour product, starch product, premixed product, noodle, macaroni, bread, bean jam, buckwheat noodle, wheat-gluten bread, rice noodle, gelatin noodle and packed rice cake), products of processed fat and oil (e.g., plastic fat and oil, tempura oil, salad oil, mayonnaise and dressing), products of processed soybeans (e.g., tofu, miso and fermented soybean), products of processed meat (e.g., ham, bacon, pressed ham and sausage), processed marine products (e.g., frozen ground fish, boiled fish paste, tubular roll of boiled fish paste, cake of ground fish, deep-fried patty of fish paste, fish ball, sinew, fish meat ham or sausage, dried bonito, product of processed fish egg, canned marine product and fish boiled in sweetened soy sauce), dairy products (e.g., raw milk, cream, yogurt, butter, cheese, condensed milk, powdered milk and ice cream), products of processed vegetables and fruits (e.g., paste, jam, pickle, fruit juice, vegetable drink and mixed drink), confectioneries (e.g., chocolate, biscuit, sweet bun, cake, rice-cake sweet and rice sweet), alcohol drinks (e.g., sake, Chinese liquor, wine, whisky, shochu, vodka, brandy, gin, rum, beer, soft alcohol drink, fruit liquor and liqueur), luxury drinks (e.g., green tea, tea, oolong tea, coffee, soft drink and lactic acid drink), seasonings (e.g., soy sauce, sauce, vinegar and sweet sake), canned, bottled or bagged foods (e.g., various cooked foods such as rice topped with cooked beef and vegetables, rice boiled together with meat and vegetables in a small pot, steamed rice with red beans, and curry), semi-dried or condensed foods (e.g., liver paste, other spreads, soup for buckwheat noodle or udon and condensed soup), dried foods (e.g., instant noodle, instant curry, instant coffee, powdered juice, powdered soup, instant miso soup, cooked food, cooked drink and cooked soup), frozen foods (e.g., sukiyaki, chawan-mushi, grilled eel, hamburger steak, shao-mai, dumpling stuffed with minced pork, various stick-shaped foods and fruit cocktail), solid or liquid foods (e.g., soup), processed agricultural or forest products (e.g., spice), processed livestock products, processed marine products and the like.

As long as the food or drink of the present invention contains, is produced by adding thereto and/or is produced by diluting at least one member selected from the group consisting of a compound selected from the compounds of formulas I to IX and a soluble saccharide containing the compound at its reducing end, for example, a saccharide prepared by acid decomposition under acidic conditions below pH 7 and/or enzymatic digestion of a raw substance (e.g., a saccharide such as agarobiose, agarotetraose, agarohexaose, agarooctaose, κ-carabiose or β-D-galactopyranosyl-3,6-anhydro-2-O-methyl-L-galactose) in an amount necessary for exhibiting its physiological function, its form is not limited to a specific one. The foods or drinks may be in any edible forms such as tablets, granules and capsules.

3,6-Anhydrogalactopyranose, a 2-O-methylated derivative and a 2-O-sulfated derivative thereof, and the saccharides containing these compounds at their reducing ends tend to open at their hemi-acetal rings to form aldehyde groups at the ends. These aldehyde groups as well as the aldehyde groups of the aldehydes of 3,6-anhydrogalactopyranose tend to react with compounds which are reactive with aldehyde groups, for example, nucleophiles such as amino acids. The compounds of formulas I to IX or the saccharides (e.g., oligosaccharides) thus reacted lose the compounds selected from the compounds of formulas I to IX at their reducing ends. Therefore, they lose various physiological activities of the compounds of formulas I to IX or the oligosaccharides containing the compounds at their reducing ends. That is, in order to stably maintain the member selected from the group consisting of a compound selected from the compounds of formulas I to IX and a saccharide containing the compound at its reducing end in a food or a drink, the molar concentration of the compound reactive with the aldehyde should be kept lower than that of the aldehyde.

In the production of the food or drink of the present invention, it is possible to provide a food or a drink that contains a member selected from the group consisting of a compound selected from the compounds of formulas I to IX and an oligosaccharide containing the compound at its reducing end at a high concentration without substantially reducing the amount thereof by controlling the amount of a compound reactive with the aldehyde. Such control has not been considered heretofore in the prior art.

It is also found that the compound selected from the compounds of formulas I to IX, and the compound selected from the compounds of formulas I to IX located at the reducing end of the saccharide containing the compound at its reducing end are stable under acidic conditions. Then, an acidic food or acidic drink which contains at least one member selected from the group consisting of a compound selected from the compounds of formulas I to IX and a soluble saccharide containing the compound at its reducing end at a high concentration can be provided by carrying out all of the steps of producing the food or drink of the present invention under acidic conditions to prepare the acidic food or acidic drink.

In addition, a compound selected from the compounds of formulas I to IX and a soluble saccharide containing the compound at its reducing end (e.g., agarooligosaccharide derived from agar) inhibit the production of inflammatory mediators (e.g., NO and prostaglandin $E_2$ ($PGE_2$)) induced by lipopolysaccharide (LPS), TPA or the like. Thus, the compound is also useful as an additive for foods for preventing carcinogenesis.

No acute toxicity was observed when a member selected from the group consisting of a compound selected from the compounds of formulas I to IX and a soluble saccharide containing the compound used in the present invention was orally or intraperitoneally administered to a mouse at a dosage of 1 g/kg.

EXAMPLES

The following Referential Examples and Examples further illustrate the present invention in detail but are not to be construed to limit the scope thereof.

Referential Example 1

Agar (Agar Noble) was suspended in 0.1N HCl at a concentration of 10% and heated at 100° C. for 19 minutes.

10 ml of the above-mentioned sample was applied to TOYOPEARL HW40C (Tosoh) column (4.4 cm×85 cm) equilibrated with water. Gel filtration chromatography was carried out using water as a mobile phase at a flow rate of 1.4 ml/min. The eluted substances were detected using a differential refractometer. Each of the collected fractions contained 7 ml of the eluate.

Peaks were observed at elution time 406, 435, 471 and 524 minutes. Analysis of the fractions corresponding to the respective peaks revealed that substances contained in the fractions were agarooctaose, agarohexaose, agarotetraose and agarobiose in this order. The analysis was carried out by spotting the fractions onto a silica gel 60 sheet $F_{254}$ (Merck), developing using 1-butanol:ethanol:water=5:5:1, and analyzing according to the orcinol-sulfuric acid method. The fractions were lyophilized to obtain 30 mg of agarooctaose, 100 mg of agarohexaose, 150 mg of agarotetraose and 140 mg of agarobiose.

Referential Example 2

(1) A mixture containing 150 g of commercially available agar (Ina agar type S-7, Ina Shokuhin Kogyo), 15 g of citric acid (anhydrate) for food additives (San-Ei Gen F.F.I.) and deionized water to 1.5 liter was heated to 92° C., and then incubated at 92–95° C. for 130 minutes while stirring. The mixture was then cooled to room temperature and filtered using body feed of 0.5% of Celite 545 (Celite) to prepare a filtrate (agar decomposition oligosaccharide solution). The filtrate was analyzed by normal phase HPLC as follows.

Column: PALPAK type S (4.6×250 mm, Takara Shuzo, CA8300);
Solvent A: aqueous 90% acetonitrile solution;
Solvent B: aqueous 50% acetonitrile solution;
Flow rate: 1 ml/min.;
Elution: Solvent A (10 min.)→linear gradient from Solvent A to Solvent B (40 min.)→Solvent B (10 min.);
Detection: absorbance at 195 nm;
Column temperature: 40° C.

As a result, it was confirmed that agarobiose, agarotetraose, agarohexaose and agarooctaose were mainly generated as saccharaides.

In addition, similar results were obtained by conducting normal phase HPLC and gel filtration HPLC under the following conditions.

(a)
Column: TOSOH TSK-gel Amide-80 (4.6×250 mm, Tosoh)
Solvent: 60% $CH_3CN$;
Flow rate: 0.7 mL/min.;
Detection: RI detector;
Column temperature: 80° C.

(b)
Column: TOSOH TSK-gel ALPHA-2500×2 (7.8×300 mm, Tosoh);
Solvent: $H_2O$;
Flow rate: 0.3 mL/min.;
Detection: RI detector;
Column temperature: 60° C.

The pH of the filtrate was about 2.6. The filtrate had an acidity of 0.92 and Brix of 9.2%. The amount of produced agarobiose measured as described in Referential Example 2-(2) was 43.1 mM.

(2) Agarobiose was quantified using F-kit lactose/galactose (Boehringer Mannheim, code 176303) by measuring the concentration of galactose generated from agarobiose by the action of β-galactosidase.

The quantification was carried out according to the instructions attached to the kit except that β-galactosidase was reacted at 37° C. for 1 hours. A calibration curve was prepared using lactose. A molar concentration for lactose (mM) was calculated, which was then converted to a corresponding agarobiose concentration (mg/ml).

Quantification of agarobiose, agarotetraose, agarohexaose and agarooctaose prepared in Referential Example 1 was examined according to the above-mentioned method. As a result, the calculated value for agarobiose was consistent with the actually determined value. On the other hand, agarotetraose, agarohexaose or agarooctaose was not substantially detected by the above-mentioned method. Thus, it was demonstrated that agarooligosaccharides other than agarobiose were not detected by the above-mentioned detection method substantially. Accordingly, the concentration of agarobiose among agarooligosaccharides can be measured using the above-mentioned method.

Referential Example 3

Commercially available agar (Ina agar type S-7, Ina Shokuhin Kogyo) was dissolved in desalted water at a concentration of 10% w/v. A strong cation exchange resin active type ($H^+$) (Diaion, SK-104, Mitsubishi Chemical Corporation) was added thereto at a concentration of 1% w/v. The mixture was subjected to hydrolysis at 95° C. for 3 hours. After reaction, the mixture was cooled to normal temperature to separate solid from liquid (to remove the resin from the solution). The resulting solution was treated with active carbon at a concentration of 4% w/v to remove colored substances and the like. After filtration using a filter having a pore size of 0.1 μm, the filtrate was concentrated under reduced pressure, filtrated again using a filter having a pore size of 0.2 μm, and lyophilized according to a conventional method to prepare agabiose as a composition containing agarobiose.

The composition of the agabiose was as follows: 1.3% water; 3.4% galactose; 30.7% agarobiose; 62.4% agarooligosaccharides such as agarotetraose and agarohexaose. The pH was 4.1.

Example 1

RAW264.7 cells (ATCC TIB 71) were suspended in Dulbecco's modified Eagle's medium (Bio Whittaker, 12-917F) without Phenol Red containing 10% fetal calf serum and 2 mM L-glutamine (Life Technologies Oriental, Code. 25030-149) at a concentration of 3×10⁵ cells/ml. 500 μl of the suspension was added to each well of a 48-well microtiter plate and the plate was incubated at 37° C. for 6 hours in the presence of 5% $CO_2$. 10 μl of a filter-sterilized oligosaccharide solution containing agarobiose, agarotetraose or agarohexaose prepared in Referential Example 1 at a concentration of 5 mM in water was added to the well. The plate was incubated for additional 0.5 or 5 hours. 10 μl of aqueous solution containing lipopolysaccharide (LPS, Sigma, Code. L-2012) at a concentration of 5 μg/ml and interferon-γ (IFN-γ, sold by Cosmobio, Code. GZM-MG-IFN) at a concentration of 2000 U/ml was added to the well. The plate was incubated for additional 12 hours. The concentration of $NO_2^{31}$ resulting from oxidation of NO in the medium was then measured.

As control groups, a group to which LPS or IFN-γ was not added and a group to which agarobiose, agarotetraose or agarohexaose was not added were provided.

After cultivation, 100 μl of 4% Griess' reagent (Sigma, Code. G4410) was added to 100 μl of the culture supernatant, and the mixture was allowed to stand for 15 minutes at room temperature. The absorbance at 490 nm was then measured. $NO_2^-$ concentration in the medium was calculated with reference to a calibration curve prepared by using $NaNO_2$ dissolved in the same medium at a predetermined concentration. All of the measurements were carried out in triplicate.

As a result, agarobiose, agarotetraose and agarohexaose inhibited NO production induced by LPS and IFN-γ. A stronger activity of inhibiting NO production was observed for the cells cultured for 5 hours in the presence of an agarooligosaccharide before the addition of LPS and IFNγ as compared with the cells cultured for 0.5 hour. Furthermore, a stronger activity of inhibiting NO production was observed for a longer sugar chain, i.e., agarobiose<agarotetraose<agarohexaose. The results are shown in FIG. 1. FIG. 1 illustrates the $NO_2^-$ concentration in a culture medium obtained by culturing under various culture conditions. In FIG. 1, the horizontal axis represents the culture conditions and the vertical axis represents the $NO_2^{31}$ concentrations (μM).

Example 2

HL-60 cells were added to RPMI 1640 medium (Bio Whittaker, Code. 12-702F) containing 10% fetal calf serum and 1.3% dimethyl sulfoxide (Dojindo Laboratories, Code. 346-03615) and cultured at 37° C. for 1 week in the presence of 5% $CO_2$ to prepare cells differentiated into neutrophil-like cells (hereinafter referred to as HL-60 Nu).

Agarobiose, agarotetraose or agarohexaose obtained in Referential Example 1 was dissolved in water at a concentration of 5 mM. The solution was sterilized by filtration. HL-60 Nu cells were suspended in RPMI 1640 medium containing 10% fetal calf serum at a concentration of $2.5×10^5$ cells/2.4 ml. 50 μl of one of the oligosaccharide aqueous solutions was added to a well containing the cells. The cells were cultured at 37° C. for 2 hours in the presence of 5% $CO_2$. Then, 50 μl of a solution containing phorbol 12-myristate 13-acetate (TPA, Gibco, Code. 13139-019) at a concentration of 5 mg/ml in water was added the well. After the cells were cultured for additional 5 hours, intracellular peroxides were determined. As control groups, a group to which TPA was not added and a group to which agarobiose, agarotetraose or agarohexaose as not added were provided.

After cultivation, 10 μl of a solution containing 2',7'-dichlorofluorescein diacetate (Sigma, Code. D6833) at a concentration of 5 mM in dimethyl sulfoxide was added to the well. The cells were cultured for additional 30 minutes. The cells were then collected by centrifugation and washed twice in phosphate buffered saline. 2',7'-dichlorofluorescein, which is generated in proportion to the amount of intracellular peroxides, was determined using FACScan as described in Saibo Kogaku, Bessatsu (Cell Technology, Suppl.) Jikken Protocol Series: Kassei Sanso Jikken Protocol (Experimental Protocol Series: Experimental Protocols for Active Oxigen) (1994, Shujun-sha) pp. 51–54.

Figure 2:
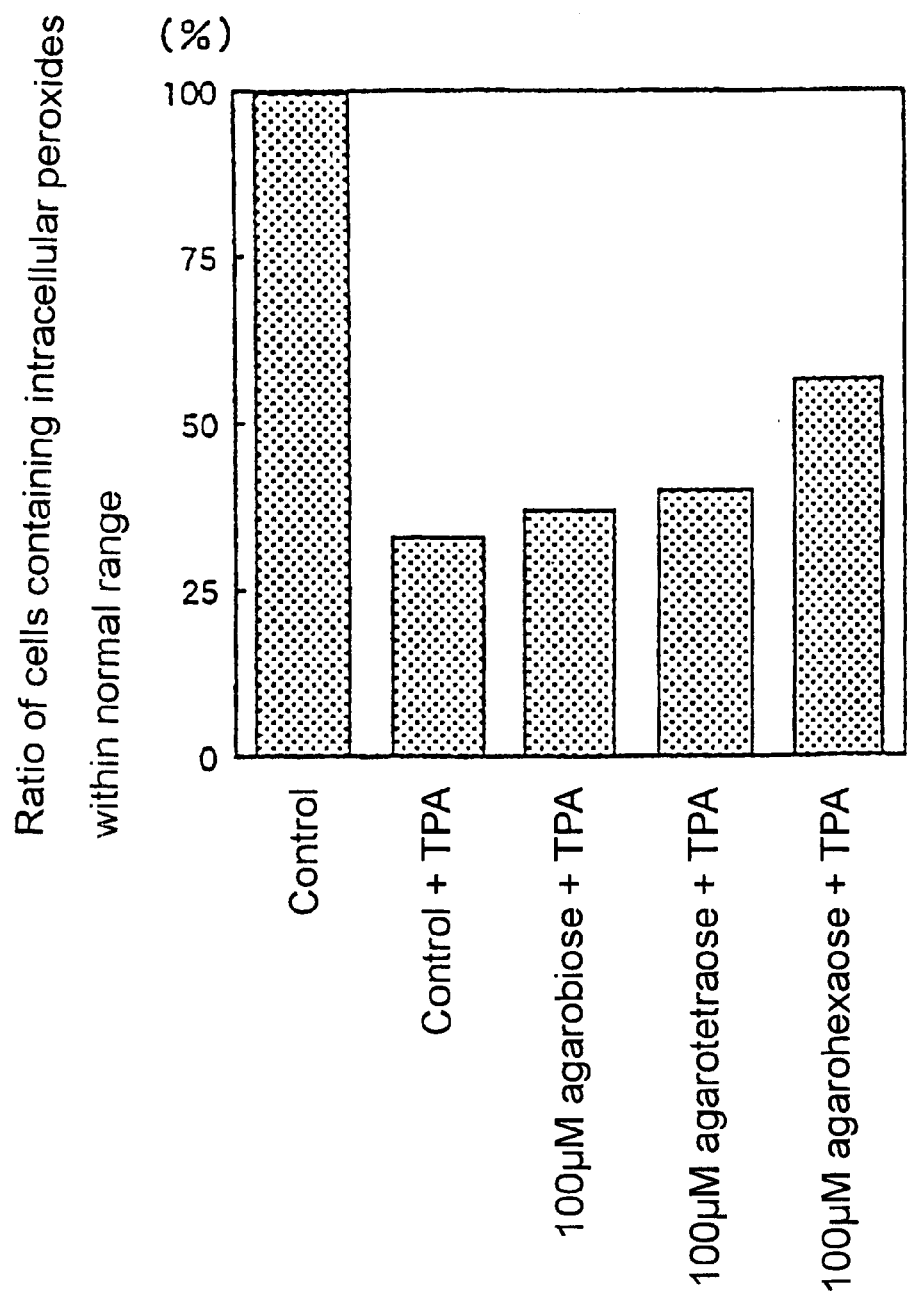
FIG. 2 illustrates the ratio (%) of cells containing intracellular peroxides within a normal range in a culture medium obtained by culturing under various culture conditions with the addition of agarobiose, agarotetraose or agarohexaose.

As a result, inhibition of TPA-induced generation of intracellular peroxides was observed for agarohexaose. Slight inhibition was also observed for agarobiose and agarotetraose. The results are shown in FIG. 2. FIG. 2 illustrates the ratio of cells containing intracellular peroxides within a normal range obtained by culturing under various culture conditions. The horizontal axis represents the culture conditions. The vertical axis represents the ratio (%) of cells containing intracellular peroxides within a normal range.

Example 3

RAW264.7 cells (ATCC TIB 71) were suspended in Dulbecco's modified Eagle's medium (Bio Whittaker, Code. 12-604F) containing 10% fetal calf serum at a concentration of $3×10^5$ cells/ml. 500 μl of the suspension was added to each well of a 48-well microtiter plate and the plate was incubated at 37° C. for 6 hours in the presence of 5% $CO_2$. 10 μl of a filter-sterilized agarooligosaccharide solution containing agarobiose, agarotetraose or agarohexaose prepared in Referential Example 1 at a concentration of 5 mM in water was added to the well. The plate was incubated for additional 0.5 or 5 hours. 10 μl of 50 μg/ml LPS aqueous solution was then added to the well. After the plate was incubated for additional 12 hours, the amount of prostaglandin $E_2$ was measured. As control groups, a group to which LPS was not added and a group to which agarobiose, agarotetraose or agarohexaose was not added were provided.

After cultivation, the amount of prostaglandin $E_2$ in the culture supernatant was measured using Prostaglandin $E_2$ ELISA Kit (Neogen, Code. 404110). All of the measurements were carried out in triplicate.

Figure 3:
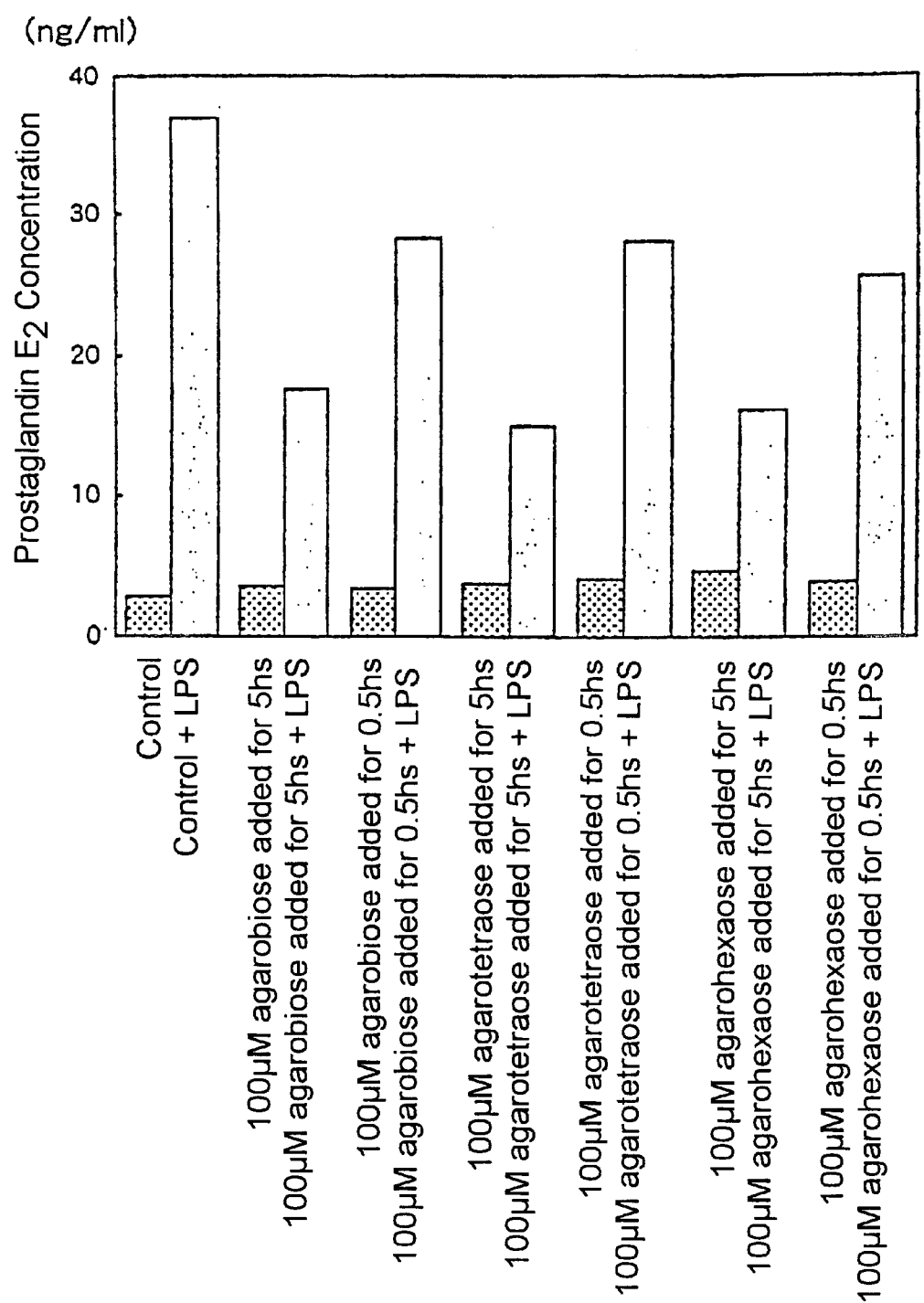
FIG. 3 illustrates the prostaglandin $E_2$ concentration in a culture medium obtained by culturing under various culture conditions with the addition of agarobiose, agarotetraose or agarohexaose.

As a result, agarobiose, agarotetraose and agarohexaose inhibited the prostaglandin $E_2$ production induced by LPS. A stronger activity of inhibiting prostaglandin $E_2$ production was observed for the cells cultured for 5 hours in the presence of an agarooligosaccharide before the addition of LPS as compared with the cells cultured for 0.5 hour. The results are shown in FIG. 3. FIG. 3 illustrates the prostaglandin $E_2$ concentration in the medium obtained by incubating under various culture conditions. In FIG. 3, the horizontal axis represents the culture conditions and the vertical axis represents the prostaglandin $E_2$ concentration (ng/ml).

Example 4

(1) 8.5 g of calcium carbonate (Wako Pure Chemical Industries, Code. 034-00425) was added to 1 liter of the agar decomposition oligosaccharide solution prepared in Referential Example 2. The mixture was stirred overnight at 5° C. and then filtered to obtain a filtrate. By this treatment, the citric acid concentration changed from 11.40 mg/ml to 1.37 mg/ml, and the calcium concentration changed from 0.25 mg/ml to 0.62 mg/ml.

(2) The agar decomposition oligosaccharide solution from which citric acid was removed as described in Example 4-(1) was lyophilized to obtain powder, which was dissolved in tap water at a concentration of 10% to prepare a 10% agar oligosaccharide solution.

The 10% agar oligosaccharide solution prepared as described above was freely given as drinking water to ddy mice (Japan SLC, female, 7 weeks old) for 21 days. Tap water was freely given as a control. Each group consisted of 2 mice. Thereafter, 4 ml of RPMI 1640 medium (Bio Whittaker, Code. 12-702F) containing 10% fetal calf serum was intraperitoneally injected. Media removed from 2 mice after extensive massage were combined to obtain celiac cells. The celiac cells were suspended in RPMI 1640 medium containing 10% fetal calf serum at a concentration of $10^6$ cells/ml. 500 μl of the suspension was added to each well of a 48-well microtiter plate and the plate was incubated at 37° C. for 2 hours in the presence of 5% $CO_2$. Adhesive cells obtained by removing the culture supernatant were used as celiac macrophages. 500 μl of fresh Dulbecco's modified Eagle's medium (Bio Whittaker, Code. 12-917F) without Phenol Red containing 10% fetal calf serum and 2 mM L-glutamine was added to each well. 10 μl of aqueous solution containing LPS at a concentration of 5 μg/ml and IFN-γ at a concentration of 2000 U/ml was added to the well. The plate was incubated for additional 12 hours. The concentration of $NO_2^-$ resulting from oxidation of NO in the medium was then measured as described in Example 1. As a control group, a group to which the aqueous solution of LPS and IFN-γ was not added was provided. All of the measurements were carried out in triplicate.

As a result, a remarkable activity of inhibiting NO production was observed for the celiac macrophages prepared from mice to which the 10% agar oligosaccharide solution was freely given. The agar oligosaccharide exhibited a strong activity of inhibiting NO production when freely given as drinking water.

Figure 4:
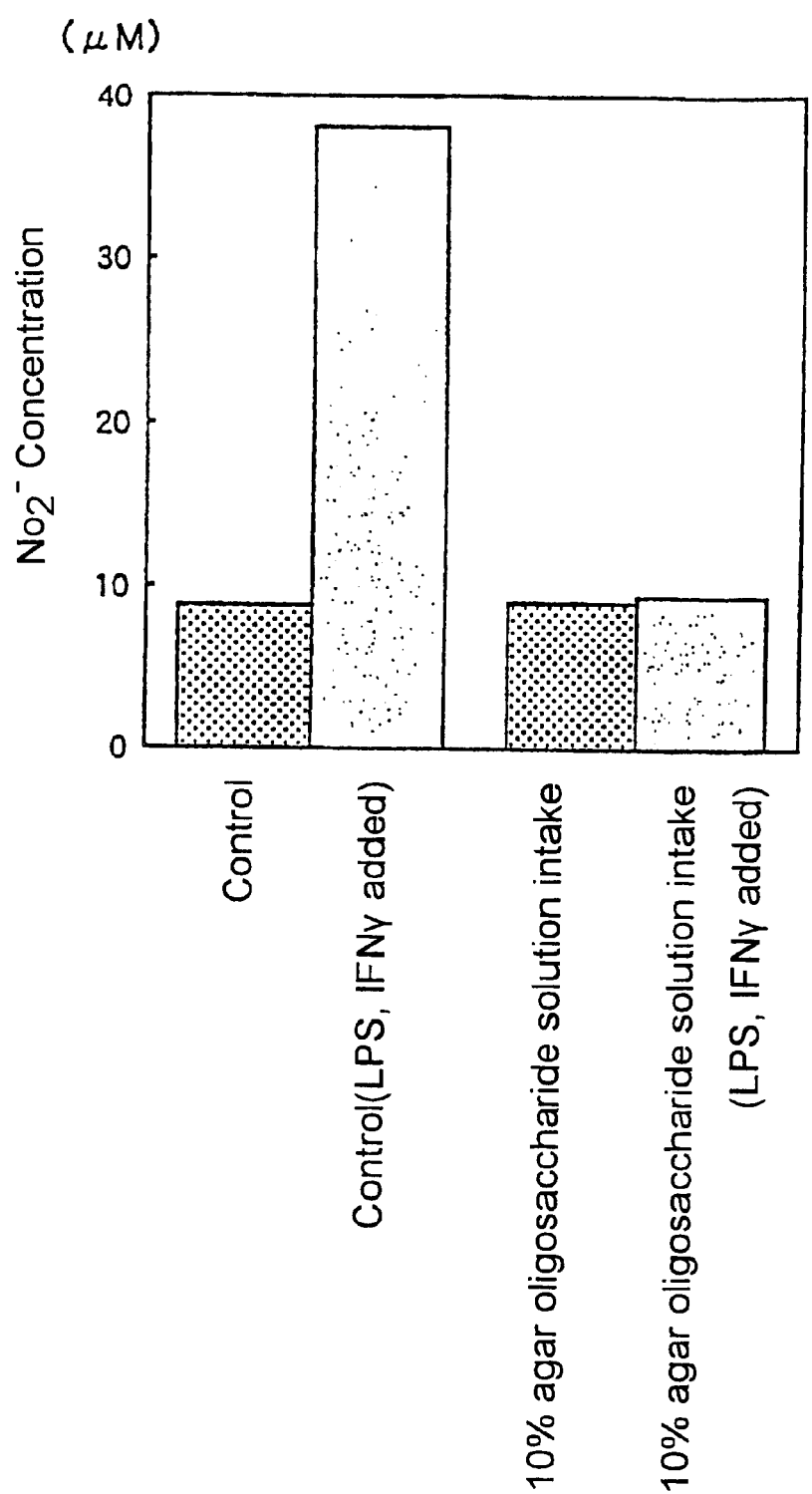
FIG. 4 illustrates the $NO_2^{31}$ concentration in a culture medium obtained by culturing under various culture conditions.

The results are shown in FIG. 4. FIG. 4 illustrates the $NO_2^-$ concentration in a culture medium obtained by culturing under various culture conditions. The horizontal axis represents the culture conditions and the vertical axis represents the $NO_2^-$ concentrations (μM)

Example 5

The agar decomposition oligosaccharide solution from which citric acid was removed as described in Example 4-(1) was lyophilized to obtain powder, which was dissolved in tap water at a concentration of 10% to prepare a 10% agar oligosaccharide solution.

The 10% agar oligosaccharide solution prepared as described above was freely given as drinking water to ddy mice (Japan SLC, female, 7 weeks old) for 21 days. Tap water was freely given as a control. Each group consisted of 2 mice. Thereafter, 4 ml of RPMI 1640 medium (Bio Whittaker, Code. 12-702F) containing 10% fetal calf serum was intraperitoneally injected. Media removed from 2 mice after extensive massage were combined to obtain celiac cells. The celiac cells were suspended in RPMI 1640 medium containing 10% fetal calf serum at a concentration of $10^6$ cells/ml. 500 μl of the suspension was added to each well of a 48-well microtiter plate and the plate was incubated at 37° C. for 2 hours in the presence of 5% $CO_2$. Adhesive cells obtained by removing the culture supernatant were used as celiac macrophages. 500 μl of fresh Dulbecco's modified Eagle's medium (Bio Whittaker, Code. 12-604F) containing 10% fetal calf serum was added to each well. 10 μl of an aqueous solution containing LPS at a concentration of 50 μg/ml was added to the well. The plate was incubated for additional 12 hours. The amount of prostaglandin $E_2$ was then measured. As a control group, a group to which LPS was not added was provided.

After cultivation, the amount of prostaglandin $E_2$ in the culture supernatant was measured using Prostaglandin $E_2$ ELISA Kit. All of the measurements were carried out in triplicate.

As a result, a remarkable activity of inhibiting prostaglandin $E_2$ production was observed for the celiac macrophages prepared from mice to which the 10% agar oligosaccharide solution was freely given. The agar oligosaccharide exhibited a strong activity of inhibiting prostaglandin $E_2$ production when freely given as drinking water.

Figure 5:
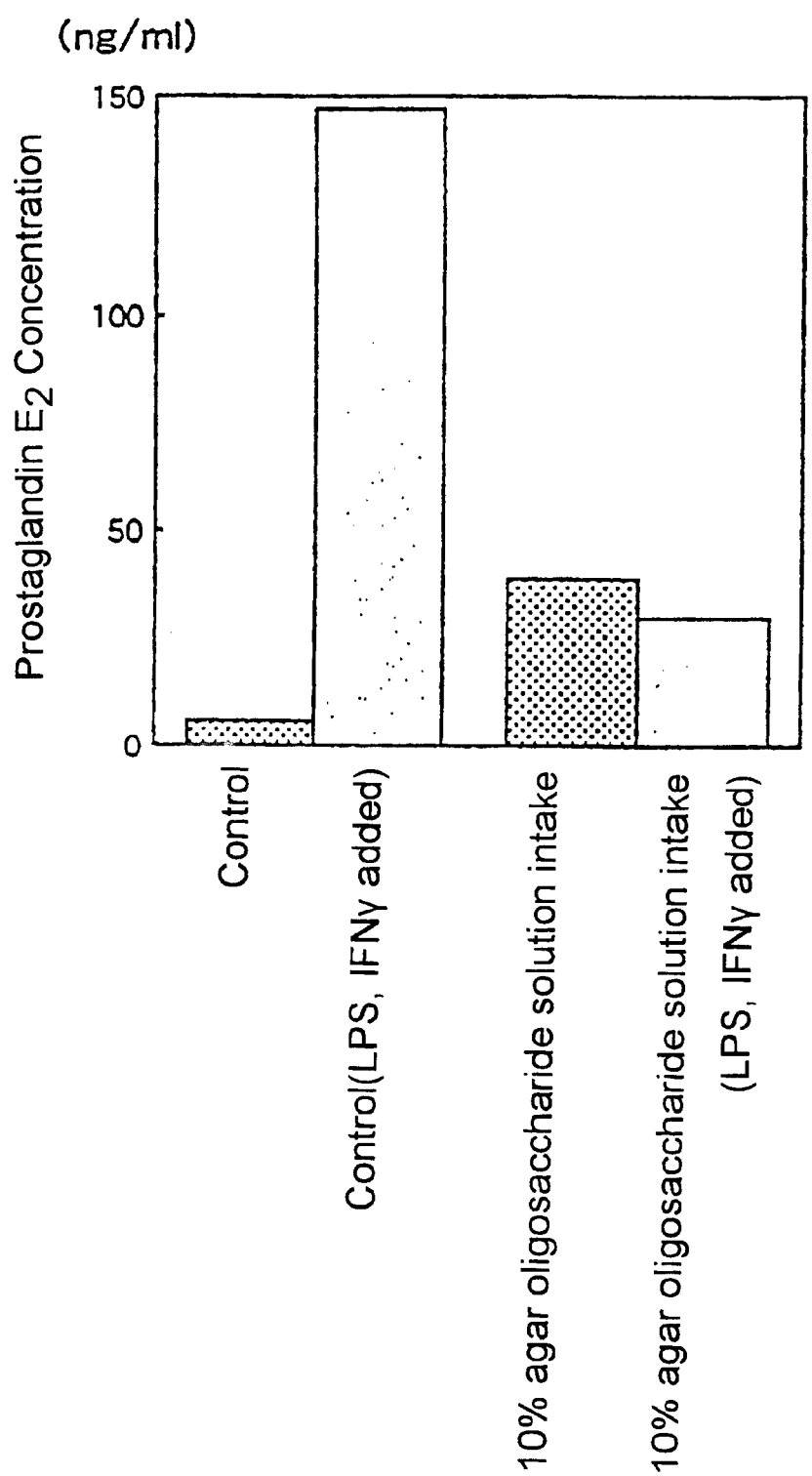
FIG. 5 illustrates the prostaglandin $E_2$ concentration in a culture medium obtained by culturing under various culture conditions.

The results are shown in FIG. 5. FIG. 5 illustrates the prostaglandin $E_2$ concentrations in a culture medium obtained by culturing under various culture conditions. The horizontal axis the represents the culture conditions and the vertical axis represents the prostaglandin $E_2$ concentration (ng/ml)

Example 6

(1) An α-glucosidase activity was measured by allowing α-glucosidase to act on p-nitrophenyl-α-D-glucopyranoside (a chromogenic substrate) and calorimetrically quantifying 4-nitrophenol released by hydrolysis.

10 μl of α-glucosidase solution [40 mU/ml, derived from S. cerevisiae, Sigma, dissolved in 10 mM phosphate buffer (pH 7.2 at 37° C.)] and 10 μl of a solution containing a test sample dissolved in 10 mM phosphate buffer (pH 7.2 at 37° C.) were mixed. 80 μl of a 1.5 mg/ml substrate solution [Sigma, dissolved in 10 mM phosphate buffer (pH 7.2 at 37° C.)] was added thereto to initiate the reaction. After reacting at 37° C. for 40 minutes, the absorbance at 410 nm was measured using Shimadzu uv2200. The results are shown in Table 1. The remaining activity therein was calculated defining the activity observed without the addition of test sample as 100%.

TABLE 1

Activity of inhibiting α-glucosidase (% remaining activity)

| | 0 μM | 5 μM | 50 μM | 500 μM | 1000 μM | 5000 μM |
|---|---|---|---|---|---|---|
| Anhydrogalactose | 100 | 100 | 100 | 100 | 100 | 100 |
| Agarobiose | 100 | 100 | 100 | 100 | 100 | 100 |
| Agarotetraose | 100 | 100 | 97 | 75 | 32 | 20 |
| Agarohexaose | 100 | 91 | 91 | 47 | 35 | 7 |
| Agarooctaose | 100 | 91 | 90 | 32 | 26 | 11 |
| Neoagarobiose | 100 | 100 | 100 | 100 | 100 | 100 |
| Neoagarotetraose | 100 | 100 | 93 | 89 | 76 | 42 |
| Neoagarohexaose | 100 | 100 | 100 | 93 | 71 | 8 |

These results demonstrated that agarooligosaccharides of 4 saccharides or more and neoagarooligosaccharides of 4 saccharides or more have activities of inhibiting α-glucosidase. In addition, it was demonstrated that agarooligosaccharides have stronger activities of inhibiting α-glucosidase than neoagarooligosaccharides.

Agarobiose, agarotetraose, agarohexaose and agarooctaose used as test samples were those prepared in Referential Example 1. Commercially available products of anhydrogalactose (Funakoshi), neoagarobiose (Sigma), neoagarotetraose (Funakoshi) and neoagarohexaose (Funakoshi) were used.

(2) A crude enzyme preparation obtained from rat small intestine mucous membrane prepared according to the method as described in Arne Dahlqvist, Anal. Biochem., 7:18–25 (1964) was used to measure the activity of inhibiting α-glucosidase of agarotetraose or agarohexaose prepared in Referential Example 1 in vitro as follows.

For the enzymatic reaction, 80 μl of a solution of sucrose, maltose, trehalose or soluble starch as a substrate in 10 mM phosphate buffer (pH 7.0) at a final concentration of 100 mM (0.5% in case of soluble starch) was added to 10 μl of a test sample solution appropriately diluted with the same buffer. 10 μl of the crude enzyme solution prepared from rat small intestine was added thereto. The mixture was reacted at 37° C. for 20 minutes. The enzymatic activity was determined as follows as the amount of glucose generated in the reaction mixture: 3 ml of a reagent for glucose measurement (Wako Pure Chemical Industries) was added to the reaction mixture, reaction was carried out at 37° C. for 5 minutes, and then the absorbance at 505 nm was measured. The inhibitory activity on the digestion of each substrate was expressed as a remaining activity (%) against the control, which was calculated based on the activity measured as described above for each of four different concentrations. The remaining activities (%) on the respective substrates in the presence of agarotetraose are shown in Table 2, whereas the remaining activities (%) on the respective substrates in the presence of agarohexaose are shown in Table 3.

TABLE 2

Remaining activities on respective substrates in the presence of agarotetraose (%)

| Substrate (mM) | 0 | 0.2 | 0.5 | 1.0 | 2.0 |
|---|---|---|---|---|---|
| Sucrose | 100 | 92 | 85 | 83 | 72 |
| Maltose | 100 | 97 | 95 | 100 | 98 |
| Trehalose | 100 | 100 | 100 | 100 | 93 |
| Soluble starch | 100 | 100 | 96 | 97 | 91 |

TABLE 3

Remaining activities on respective substrates in the presence of agarohexaose (%)

| Substrate (mM) | 0 | 0.2 | 0.5 | 1.0 | 2.0 |
|---|---|---|---|---|---|
| Sucrose | 100 | 92 | 85 | 81 | 70 |
| Maltose | 100 | 98 | 100 | 91 | 92 |
| Trehalose | 100 | 100 | 100 | 100 | 93 |
| Soluble starch | 100 | 100 | 97 | 96 | 97 |

The inhibition constants (Ki) of these substances, agarotetraose and agarohexaose, for sucrose as determined using Dixon plot were 7.4 mM and 7.9 mM, respectively. When sucrose was used as a substrate, agarooligosaccharides exhibited stronger activities of inhibiting α-glucosidase than those observed when using maltose or the like as a substrate.

Example 7

An emulsion prepared by mixing 3 mg/ml type II collagen derived from bovine joint (K41: Collagen Gijutsu Kenshukai) and an equal volume of Freund's complete adjuvant (FCA) was subcutaneously administered (150 μg/0.1 ml/mouse) at a ridge portion of DBA/1J mouse (male, 6 weeks old). After 3 weeks, the mouse was boosted in a similar manner to induce type II collagen-induced arthritis.

A 3.3- or 33.3-fold dilution of the agar decomposition oligosaccharide solution in Referential Example 2-(1) with tap water was freely given as drinking water starting from the first round of sensitization with collagen (in case of the examination of preventive effects) or the booster (in case of the examination of therapeutic effects). Tap water was freely given to a control group. Each group consisted of 10 mice. Onset of arthritis was assessed by scoring as follows and expressed as [total score for diseased mice/number of mice in a group] (maximal score: 16). 0: no change; 1: swelling in one or plural fingers; 2: rubefaction and swelling observed overall; 3: severe swelling observed overall; 4: accompanying tonic change in joint.

Figure 6:
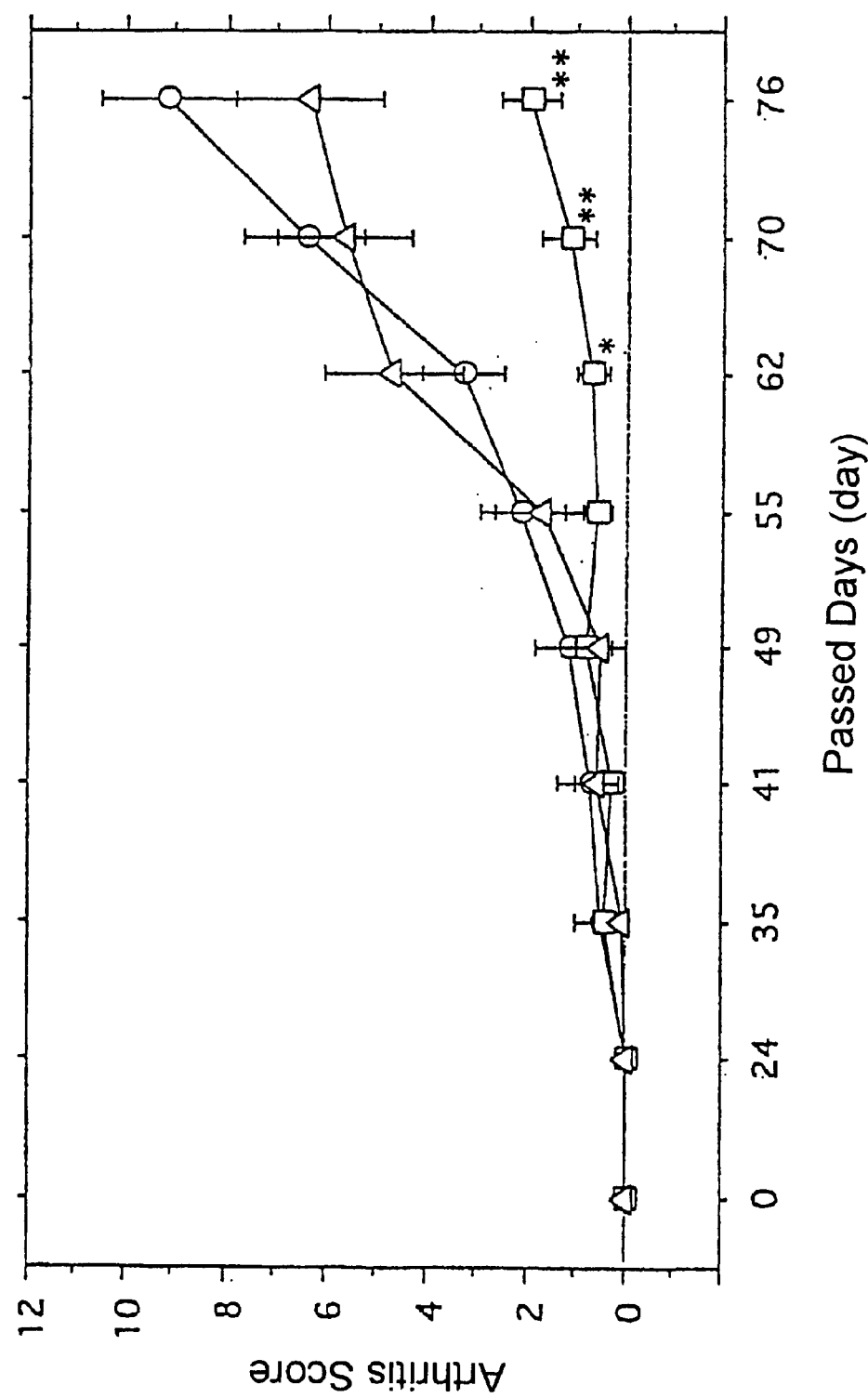
FIG. 6 illustrates the preventive effect of the oligosaccharide of the present invention on the mouse type II collagen-induced arthritis model.
Figure 7:
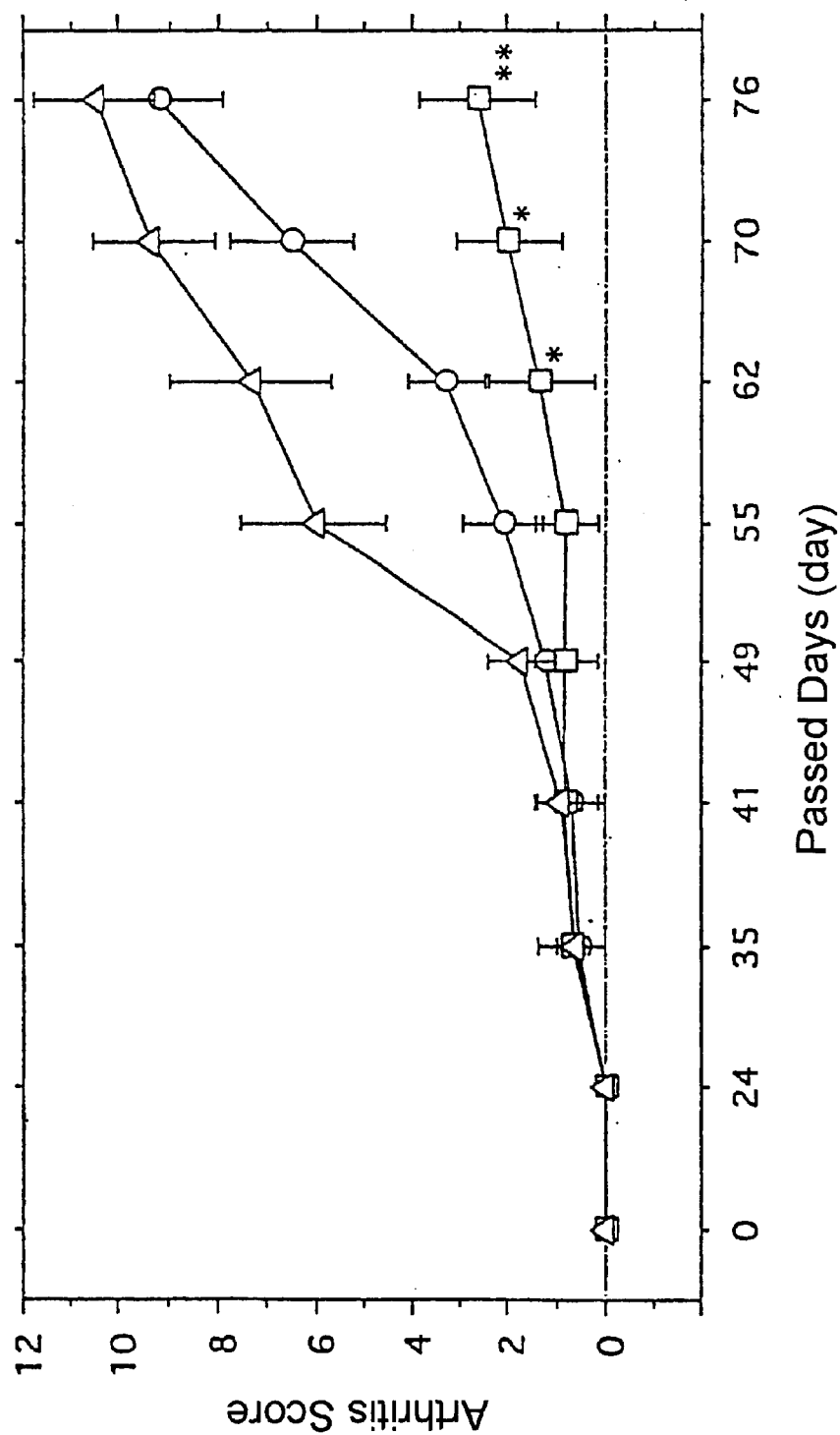
FIG. 7 illustrates the therapeutic effect of the oligosaccharide of the present invention on the mouse type II collagen-induced arthritis model.

The results are shown in FIGS. 6 and 7. The vertical axes represent the arthritis score and the horizontal axes represent the number of days passed. Each value represents mean standard variation. Open circles, open squares and open triangles represent results for the control group, the group administered with the 3.3-fold dilution and the group administered with the 33.3-fold dilution, respectively. The marks * and ** in the figures indicate significance of p<0.05 and p<0.01, respectively, against the control group as determined using Mann-Whitney U test.

Preventive effect: The average amounts of water drunk during the experimental period for the group administered with the 3.3-fold dilution and the group administered with the 33.3-fold dilution were about 130 ml/kg and about 200 ml/kg, respectively. Remarkable increase in the arthritis score was observed for the control group after day 62, whereas significant suppression was observed for the group administered with the 3.3-fold dilution.

Therapeutic effect: The average amounts of water drunk during the experimental period for the group administered with the 3.3-fold dilution and the group administered with the 33.3-fold dilution were about 150 ml/kg and about 230 ml/kg, respectively. Significant suppression was observed for the group administered with the 3.3-fold dilution after day 62.

These results demonstrate the preventive and therapeutic effects of the agar oligosaccharide on mouse type II collagen-induced arthritis. Thus, it is expected that the agar oligosaccharide would be effective for rheumatoid arthritis.

Example 8

Powder obtained by lyophilizing the agar decomposition oligosaccharide solution from which citric acid was removed as described in Example 4-(1) was dissolved in tap water at a concentration of 10%, 5% or 1% to prepare 10%, 5% and 1% agar oligosaccharide solutions. Each of the 10%, 5% and 1% agar oligosaccharide solutions was freely given as drinking water to CDF1 mouse (female, 6 weeks old). Tap water was used for dilution. Tap water was given in a similar manner to a control group. A high dose (300 μg/mouse) of LPS was intraperitoneally administered 19 days after the initiation of water drinking to create an endotoxin shock death model. The activity of suppressing mortality in 72 hours was examined [Experiment (1)]. Similarly, a low dose (20 μg/mouse) of LPS was intraperitoneally administered to a mouse 19 days after the initiation of water drinking. The serum TNF-α concentration 1 hour after the administration was measured using a commercially available ELISA kit (R & D) [Experiment (2)]. As an endotoxin hepatopathy model, a model of death due to fulminant hepatitis was created by intraperitoneally administering a mouse with galactosamine (Sigma, 20 mg/mouse) and LPS (0.01 μg/mouse) at the same time. The effect of prolonging life was examined [Experiment (3)].

The results are shown in Table 4. The amounts of agar oligosaccharide intake during the experimental period for the groups administered with 10, 5 and 1% agar oligosaccharide solutions were about 20, 9 and 2 g/kg/day, respectively. In the Experiments (1) and (3), a significant effect of suppressing the mortality was observed for the group administered with 10% agar oligosaccharide solution. In the Experiment (2), suppression of the serum TNF-α concentration was observed for the group administered with 10% agar oligosaccharide solution.

TABLE 4

| Group | (1) Mortality Dead/Total (%) | (2) TNF (μg/ml) (n) | (3) Mortality Dead/Total (%) |
|---|---|---|---|
| Control | 7/8 (88) | 10.4 ± 1.6 (4) | 8/8 (100) |
| 10% Agar oligosaccharide solution | 2/8* (25) | 7.4 ± 0.8 (4) | 4/7* (57) |
| 5% Agar oligosaccharide solution | 6/8 (75) | 12.8 ± 1.6 (4) | 7/8 (88) |
| 1% Agar oligosaccharide solution | 8/8 (100) | 11.3 ± 1.0 (4) | 8/8 (100) |

The value in the table represents mean standard variation. The mark indicate significance of p<0.05 against the control group as determined using Mann-Whitney U test.

Chemotherapy for cancer is effective, but on the other hand, it impairs biological defense system in a patient to make the patient be susceptible to infection. Under the circumstances, sepsis caused by infection with bacteria may become lethal. It was demonstrated that agar oligosaccharide not only has a carcinostatic activity without such a side effect, but also suppresses lethality due to sepsis. Experimentally, rats and mice are much more resistant to endotoxin than humans. Thus, when a disease model is created, a procedure for increasing the sensitivity beforehand is often used. A model in which galactosamine is used in combination is exemplified. This model is also recognized to be suitable as a fulminant hepatitis model. Involvement of endotoxin as one of is factors which fulminate hepatitis and worsen chronic hepatitis has been shown to be clinically important. According to the above-mentioned results, it is expected that worsening of disease states may be prevented when a patient with chronic hepatitis takes agar oligosaccharide.

Example 9

(1) A sugar loading test was carried out by loading Lewis rat (male, 13 weeks old) with sucrose.

2 g/kg of sucrose was orally administered to a rat which had been fasted for 18 hours. Blood was collected from caudal vein immediately before the administration, or 15, 30, 60 or 120 minutes after the administration. Plasma glucose concentration was measured using a measurement kit (Glu Neo Shino-Test; Shino-Test Corporation). A 3.3- or 10-fold dilution of the agar decomposition oligosaccharide solution prepared in Referential Example 2-(1) was given as drinking water starting from 4 weeks before the sugar loading test (N=5).

Tap water was given to a control group (N=2) The average amounts of water drunk in 4 weeks for the group administered with the 3.3-fold dilution and the group administered with the 10-fold dilution were 80 ml/kg/day and 100 ml/kg/day, respectively.

Figure 8:
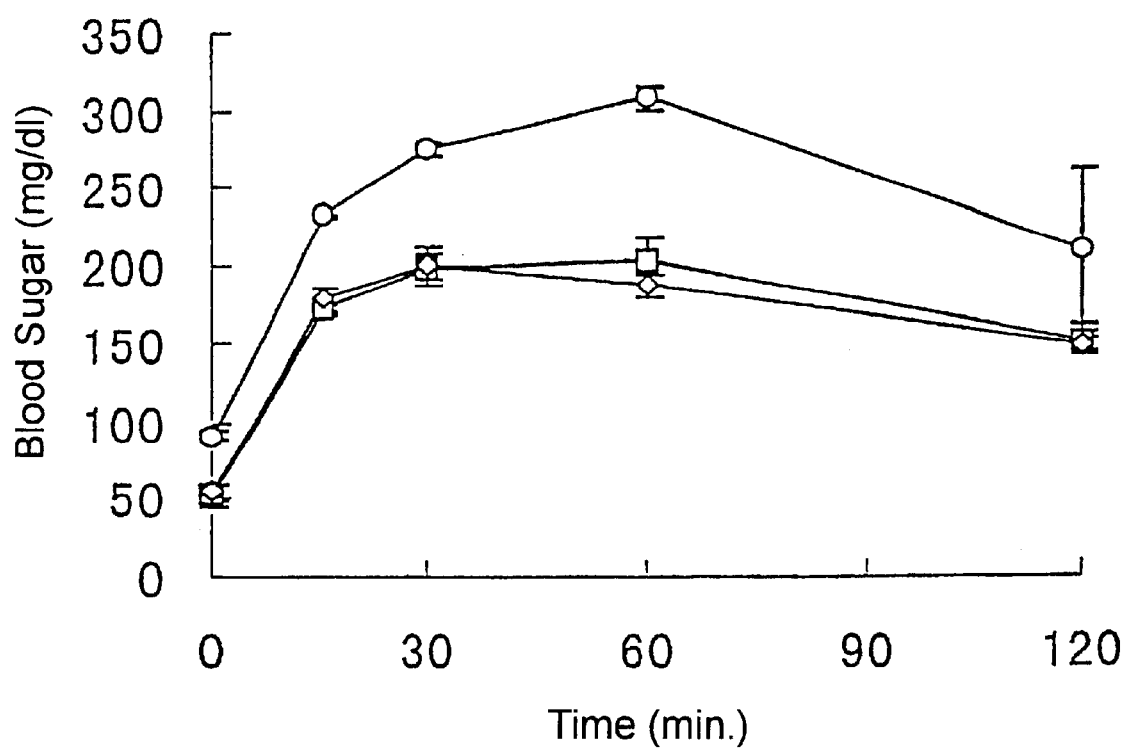
FIG. 8 illustrates the activity of inhibiting the increase in blood sugar after loading with sugar in a Lewis rat of the oligosaccharide of the present invention.

The results are shown in FIG. 8. In the figure, the horizontal axis represents the time passed after the administration of sucrose and the vertical axis represents blood sugar (mg/dl). Circles, squares and diamonds represent the changes in blood sugar for the control group, the group to which the 3.3-fold dilution was administered and the group to which the 10-fold dilution was administered, respectively.

For the control group, the blood sugar increased by 60 minutes after the loading with sugar, and decreased thereafter. It was observed that administration of agar oligosaccharide as drinking water tends to lowers the blood sugar before the loading with sugar (i.e., during the fasting) and to suppress the increase in blood sugar after the loading.

Usually, blood sugar is decreased during fasting, is transiently increased upon eating and returns to the original level as time goes by. This biological function is controlled by a hormone secreted from pancreas upon stimulation with sugar. Clinically, a test in which blood sugar is measured over time after loading with sugar during fasting is conducted in order to diagnose if the function is normal.

According to the results of the sugar loading test by loading rat with sucrose in this Example, the effectiveness of administration of agar oligosaccharide as drinking water was recognized. These results demonstrate that agar oligosaccharide has an effect on the function controlling blood sugar.

(2) A 3.3-fold dilution of the agar decomposition oligosaccharide solution prepared in Referential Example 2-(1) was given as drinking water to WBN/Kob rat (male, 59 weeks old). Tap water was given to a control group (N=3).

Blood was collected from caudal vein at intervals starting from the initiation of the administration of agar oligosaccharide. Plasma glucose concentration was measured using a measurement kit (Glu Neo Shino-Test; Shino-Test Corporation).

The average amount of water drunk during the experimental period for the group administered with the agar oligosaccharide was 300 ml/kg/day.

Figure 9:
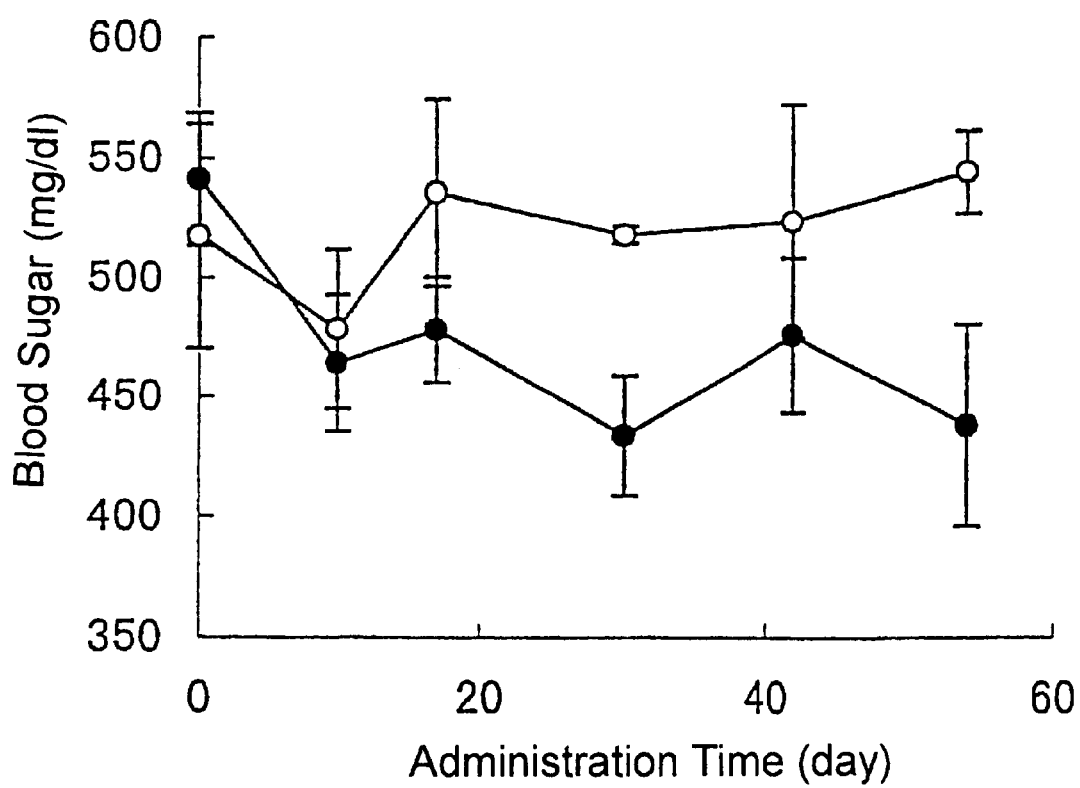
FIG. 9 illustrates the activity of decreasing blood sugar in a rat with naturally occurring diabetes of the oligosaccharide of the present invention.

The results are shown in FIG. 9. In the figure, the horizontal axis represents the number of days from the initiation of the administration and the vertical axis represents blood sugar (mg/dl). Open circles and closed circles represent the changes in blood sugar for the control group and the group to which the agar oligosaccharide was administered, respectively. During the experimental period, the control group constantly maintained the high blood glucose, whereas tendency to gradually lower the blood sugar was observed for the group administered with the agar oligosaccharide.

Inflammatory degeneration in pancreas occurs in WBN/Kob rat, a rat with naturally occurring diabetes, about 3 months after birth, and the blood sugar is increased gradually thereafter. Thus, the rat is used in experiments as a diabetes model.

The animal used in the above-mentioned experiment had very high blood sugar. Thus, it is considered that the animal had become in a severe state after several months from the onset. The effect of gradually decreasing blood sugar by the administration of agar oligosaccharide as drinking water is worthwhile for the treatment of diabetes. It is expected that it would be effective in ameliorating a severe case.

(3) A sugar loading test was carried out by loading WBN/Kob rat (male, 63 weeks old) with glucose. 2 g/kg of glucose was orally administered to a rat which had been fasted for 18 hours. Blood was collected from caudal vein immediately before the administration, or 15, 30, 60, 120 or 240 minutes after the administration. Plasma glucose concentration was measured using a measurement kit (Glu Neo Shino-Test; Shino-Test Corporation). A 3.3-fold dilution of the agar decomposition oligosaccharide solution prepared in Referential Example 2-(1) was given as drinking water starting from 4 weeks before the sugar loading test (N=3). Tap water was given to a control group (N=3). The average amount of drunk water for the group administered with the agar oligosaccharide was 300 ml/kg/day.

Figure 10:
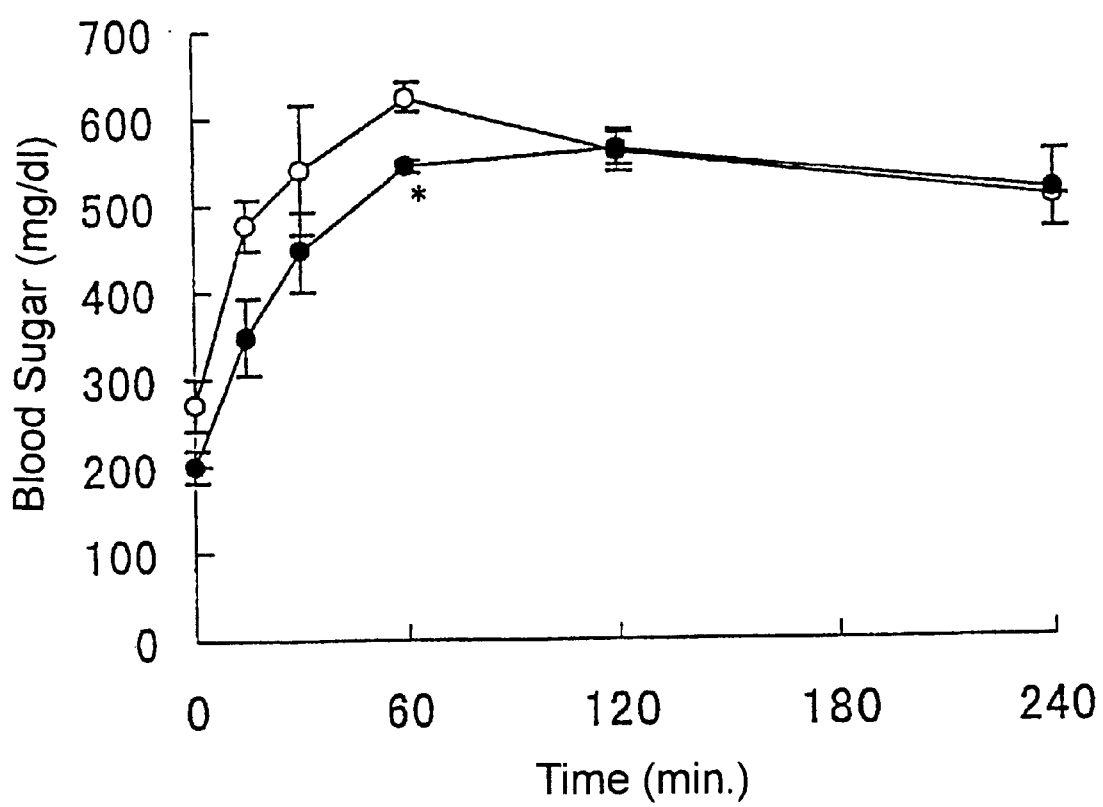
FIG. 10 illustrates the activity of inhibiting the increase in blood sugar after loading with sugar in a rat with naturally occurring diabetes of the oligosaccharide of the present invention.

The results are shown in FIG. 10. In the figure, the horizontal axis represents the time passed after the administration of glucose and the vertical axis represents blood sugar (mg/dl). Open circles and closed circles represent the changes in blood sugar for the control group and the group to which the agar oligosaccharide was administered, respectively.

For the control group, the blood sugar increased by 60 minutes after the loading with sugar, and gradually decreased thereafter. It was observed that administration of agar oligosaccharide in drinking water tends to lowers the blood sugar before the loading with sugar (i.e., during the fasting) and to suppress the increase in blood sugar after the loading. A significant effect of lowering blood sugar was observed 60 minutes after the loading with a significance level of 5% or less as compared with the control group. This tendency was maintained for 120 minutes after the loading with sugar.

Usually, blood sugar is decreased during fasting, is transiently increased upon eating and returns to the original level as time goes by. However, in the disease state of diabetes, blood sugar is not decreased even during fasting and is further increased upon eating. Blood sugar is controlled by a hormone secreted from pancreas upon stimulation with sugar. However, abnormality in this function is also observed in the disease state. Clinically, a test in which blood sugar is measured over time after loading with sugar during fasting is conducted in order to diagnose this function. According to the results of the sugar loading test by loading WBN/Kob rat, a rat with naturally occurring diabetes, with glucose in this Example, the effectiveness of administration of agar oligosaccharide as drinking water was recognized. Thus, it is expected that agar oligosaccharide would be effective in improving the function controlling blood sugar even in a disease state in which the function is abnormal.

(4) A diabetes model was created by intraperitoneally administering 120 mg/kg of streptozocin (Nacalai Tesque) to ddY mouse (male, 5 weeks old). Administration of a 3.3-, 33.3- or 333-fold dilution of the agar decomposition oligosaccharide solution prepared in Referential Example 2-(1) as drinking water was started 1 week after the administration of streptozocin. Tap water was given to a control group (N=5–6). Blood was collected from vein in eyegrounds 2, 4, 9 or 14 days after the initiation of the administration of agar oligosaccharide. Plasma glucose concentration was measured using a measurement kit (Glu Neo Shino-Test; Shino-Test Corporation).

The results are shown in Table 5. Each value in the table represents mean standard variation. The marks and in the table mean groups having significant differences with significance levels of 5% or less and 1% or less, respectively, as compared with the control group.

induced diabetes model, it is expected that the agar oligosaccharide has an anti-hyperglycemic activity.

Example 10

A solution containing TPA (Gibco) in acetone at a concentration of 5 nmol/20 $\mu$l was applied to the entire outer surface of a right auricle of an ICR mouse (male, 7 weeks old, weighing about 30g; Japan SLC). Each group consisted of 3 mice. The amount of $PGE_2$ was measured 2 hours after the application with TPA, and the auricular edema was measured 6 hours after the application with TPA.

$PGE_2$ was measured as follows. The entire auricle was excised from exsanguinated mouse. 500 $\mu$l of a extraction solution (100 mmol/l tris-hydrochloride buffer, 1 mmol/l EDTA, 2 mmol/l reduced glutathione, 2 umol/l hemoglobin) was added to the excised auricle. The mixture was homogenized. A supernatant was collected by centrifuging the homogenate at 10,000×G for 10 minutes. 500 $\mu$l of 80% ethanol and 10 $\mu$l of glacial acetic acid were added to the supernatant. The mixture was allowed to stand for 5 minutes and then centrifuged at 2,500×G for 5 minutes to collect a supernatant. The collected supernatant was applied to a C18 column and eluted using 2 ml of water and 2 ml of hexane. 4 ml of ethylacetone containing 1% methanol was added to the eluate. The ethylacetone layer was collected and evaporated to dryness using nitrogen gas. The amount of $PGE_2$ in the extract was measured using an ELISA kit (Neogen).

The auricular edema was measured by weighing the entire auricle applied with TPA excised from exsanguinated mouse.

TABLE 5

| Blood sugar (mg/dl) | Day 0 | Day 2 | Day 4 | Day 9 | Day 14 |
|---|---|---|---|---|---|
| Control (N = 6) | 286.0 ± 34.1 | 376.4 ± 60.3 | 374.0 ± 53.7 | 500.1 ± 46.5 | 546.8 ± 26.7 |
| 3.3-fold dilution (N = 5) | 272.5 ± 57.0 | 326.5 ± 79.6 | 364.3 ± 83.4 | 297.8 ± 81.4 | 373.5 ± 65.0* |
| 33.3-fold dilution (N = 6) | 255.0 ± 51.1 | 290.9 ± 62.0 | 271.4 ± 59.6 | 298.0 ± 74.3* | 361.9 ± 75.7* |
| 333-fold dilution (N = 6) | 264.4 ± 33.3 | 246.0 ± 29.5 | 238.1 ± 31.3 | 271.1 ± 55.2* | 324.1 ± 55.3** |

Blood sugar was gradually increased for the control group. A severe hyperglycemic condition was made 5 at the end of the experiment. Significant decreases in blood sugar were observed for the groups to which the 3.3-, 33.3- and 333-fold dilutions were administered 9, 9 and 14 days after the administration, respectively, as compared with the control group, and the hyperglycemic conditions observed for the control group were ameliorated.

The streptozocin-induced diabetes model is frequently used as a model which can experimentally generate a hyperglycemic condition by irreversibly damaging Langerhans' cells in pancreas. A hormone secreted from islets of Langerhans in pancreas is indispensable for controlling blood sugar. Thus, insufficient insulin secretion caused by damaging the islets becomes a factor that causes hyperglycemia.

Since the administration of agar oligosaccharide ameliorated the hyperglycemic condition in the streptozocin- The powder obtained by lyophilizing the agar decomposition oligosaccharide solution from which citric acid was removed prepared in Example 4-(1) was administered by topically applying it or by adding it in drinking water. Specifically, for topical application, a solution containing the powder at a concentration of 3% or 10% was applied to the entire outer surface of both sides of a right auricle 30 minutes before the application with TPA and air-dried. For administration as drinking water, a solution containing the powder at a concentration of 3% or 10% placed in a water-supplying bottle was freely given starting from 14 days before the application with TPA until sacrifice.

The results for the measurement of the amount of $PGE_2$ in the auricular portion are shown in Table 6.

TABLE 6

| | Amount of $PGE_2$ in auricle extract (ng/ml) mean ± standard deviation |
|---|---|
| Normal mouse (No TPA applied) | 1.1 ± 0.3 |
| Control mouse (TPA applied) | 3.1 ± 0.4 |
| Application with 10% solution of lyophilized powder | 1.9 ± 0.3 (p < 0.05 against control mouse) |
| Intake of 10% solution of lyophilized powder | 1.3 ± 0.3 (p < 0.05 against control mouse) |

As shown in Table 6, the amount of $PGE_2$ for the control group was increased by about 3-fold by applying TPA as compared with the normal mouse group. On the other hand, a significant decrease in the amount of $PGE_2$ production at the inflammation site was observed for the group to which the solution containing the lyophilized powder at a concentration of 10% was administered by applying it or by adding it in drinking water as compared with the control group. Significant difference was tested using Student's t test, and $p<0.05$ was defienned as being statistically significant.

Figure 11:
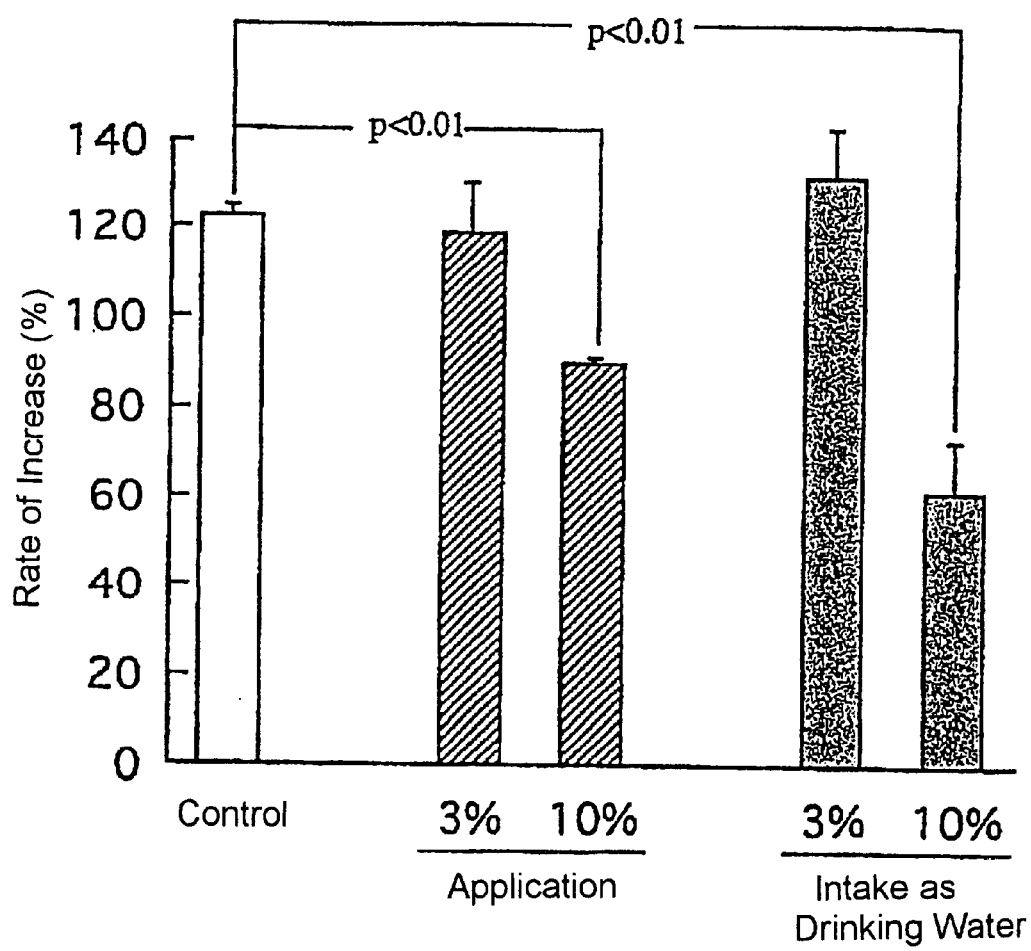
FIG. 11 illustrates the activity of inhibiting edema in a TPA-induced mouse auricular edema model of the oligosaccharide of the present invention.

The results of the weighing of the auricle portion obtained by calculating the rate of increase in the weight of auricle as compared with that without the TPA application are indicated. The results are shown in FIG. 11. In the figure, the vertical axis represents the rate of increase in the weight of auricle from a mouse with TPA application as compared with that without the TPA application. The column and the error line indicate the average value for 3 mice in a group and the standard variation, respectively. Significant difference between the control group and the group administered with the agar decomposition oligosaccharide solution from which citric acid was removed was tested using Student's t test. $p<0.05$ was defienned as being statistically significant.

The weight for the control group was increased by twice or more by applying TPA. On the other hand, a significant decrease in the increase in auricle weight was observed for the group to which the solution containing the lyophilized powder at a concentration of 10% was administered by applying it or by adding it in drinking water as compared with the control group. Thus, the activity of inhibiting edema of agar oligosaccharide was demonstrated.

Example 11

ICR mouse (female, 9 weeks old, weighing about 30 g; Japan SLC) was used. Each experimental group consisted of 10 mice. Body hair on the back of the mouse was shaved. 100 μg of 7,12-dimethylbenz[a] janthracene (DMBA; Sigma) dissolved in 100 μl of acetone was applied thereto for initiation. 1 μg of TPA (Nacalai Tesque) dissolved in 100 μp of acetone was applied to the same site for promotion twice a week for 20 weeks starting from 1 week after the initiation.

The agar decomposition oligosaccharide solution was administered by topically applying it or by adding it in drinking water. As agar decomposition oligosaccharide solutions, the agar decomposiion oligosaccharide solution in Referential Example 2-(1) (hereinafter referred to as a 10% agar oligosaccharide solution), a 3.3-fold dilution of the 10% agar oligosaccharide solution (hereinafter referred to as a 3% agar oligosaccharide solution), and a 10-fold dilution of the 10% agar oligosaccharide solution (hereinafter referred to as a 1% agar oligosaccharide solution) were used.

For topical application of the agar oligosaccharide solution, the 10% agar oligosaccharide was applied to the back 30 minutes before the application with DMBA and 30 minutes before the application with TPA, and air-dried. For administration as drinking water, the 1% or 3% agar oligosaccharide solution placed in a water-supplying bottle was freely given starting from 7 days before the application with DMBA. Tap water was given to a control group.

For each group, the number of tumors generated on the back of a mouse and the number of mice that developed tumor were scored at intervals of one week for 20 weeks from the initiation of the application with TPA.

Figure 12:
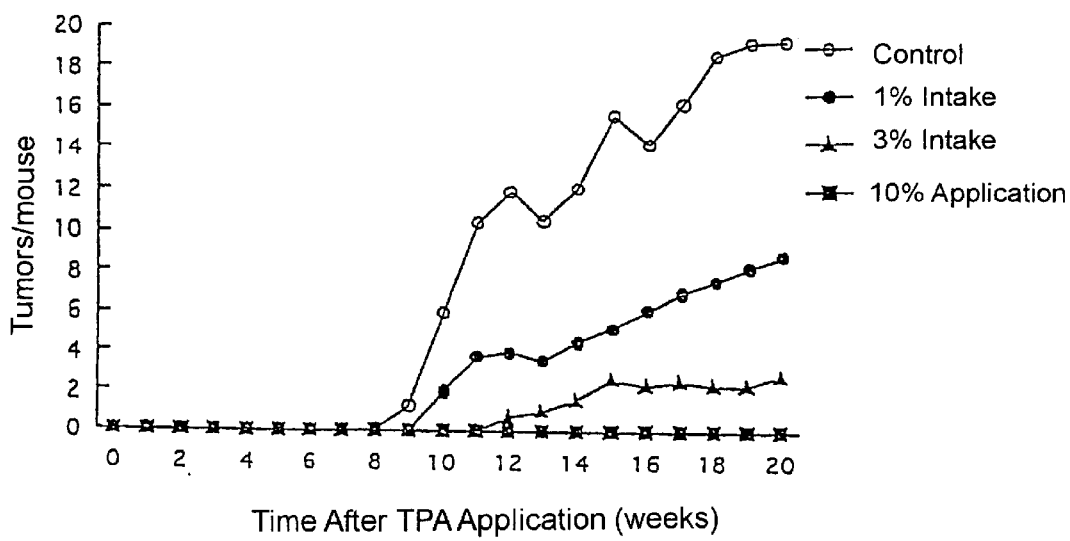
FIG. 12 illustrates the activity of inhibiting carcinogenesis in a TPA-induced mouse carcinogenesis model of the oligosaccharide of the present invention. A shows the activity on the number of tumors. B shows the activity on the incidence of tumor.
Figure 12:
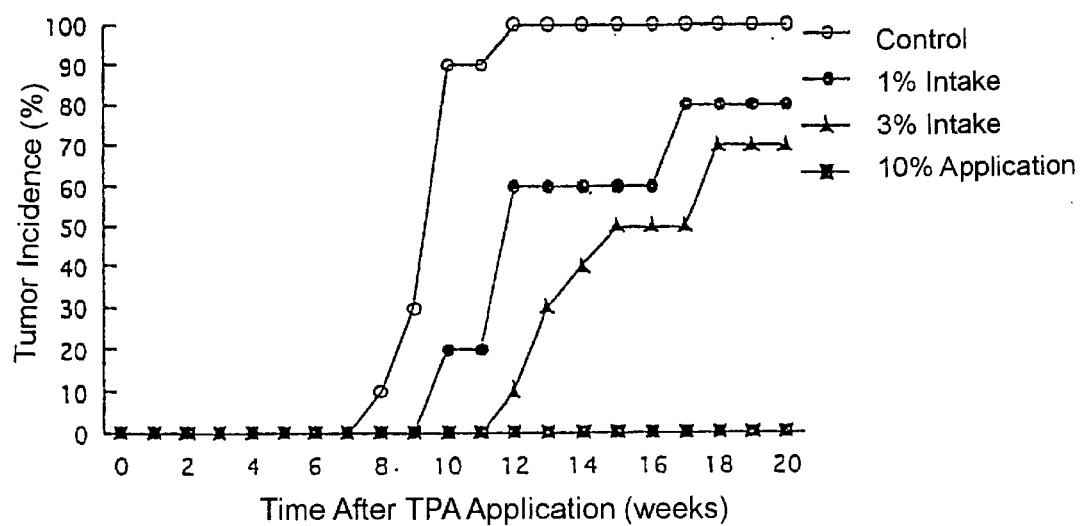

The experimental results are shown in FIG. 12. In FIG. 12, the vertical axes in A and B represent the incidence of tumor and the number of tumors developed in a mouse, respectively. The horizontal axes represent the number of weeks passed from the intiation of the application with TPA.

For the control group, development of tumor was observed for some mice 7 weeks after the initiation of the application with TPA. All of the mice developed tumor 11 weeks after the application. The average number of tumors after 20 weeks was 19.3. On the other hand, the number of tumors for the group administered with the 1% agar oligosaccharide as drinking water observed 20 weeks after the initiation was 8.8, and the number for the group administered with the 3% agar oligosaccharide solution was 2.8. Thus, a remarkable inhibitory activity was recognized. Furthermore, development of tumor was not observed at all when the 10% agar oligosaccharide solution was administered by application.

As described above, agarooligosaccharide exhibited a very strong activity of inhibiting carcinogenesis.

Example 12

DSEK cell is a fibroblast cell line established from a synovial membrane of a human patient with chronic rheumatism and is held at Department of Second Internal Medicine, Integrated Medical Center, Saitama Collage of Medicine as an in vitro rheumatoid model. DSEK cells were cultured in Iscov-MEM medium (IMDM: Gibco-BRL) containing 10% FBS (Bio Whittaker) at 37° C. in the presence of 5% $CO_2$ to saturation of culture vessel. The cells were suspended in the same medium at a concentration of $3\times10^4$ cells/ml using a trypsin-EDTA solution (Bio Whittaker). 200 μl of the suspension was dispensed into each well of a 96-well microtiter plate (Falcon). After culturing for 5 to 7 days at which time the cells grew to 80% saturation, the medium was changed to 200 μl of the above-mentioned medium containing agarobiose at a concentration of 25, 50, 75, 100, 200 or 400 μM.

10 μl of Premix WST-1 (Takara Shuzo, MK400) was added to one of the wells at intervals of 24 hours up to 72 hours after the medium change. The mixture was reacted at 37° C. for 3.5 hours. The degree of cell growth was expressed by a value obtained by subtracting the absorbance at 650 nm ($A_{650}$) from the absorbance at 450 nm ($A_{450}$).

The results are shown in Table 7.

TABLE 7

| Agarobiose Concentration ($\mu$M) | Cultivation time | | |
|---|---|---|---|
| | 24 hr | 48 hr | 72 hr |
| | Degree of cell growth ($A_{450-650}$) | | |
| 0 | 1.04 | 1.27 | 1.46 |
| 50 | 1.00 | 1.49 | 1.27 |
| 100 | 0.88 | 1.87 | 1.26 |
| 200 | 0.89 | 1.50 | 0.93 |
| 400 | 0.87 | 0.52 | 0.47 |
| 800 | 0.54 | 0.45 | 0.56 |

The concentrations that resulted in the inhibition of the growth of half cells ($IC_{50}$) at 24 hours and 72 hours as determined on the basis of the $A_{450-650}$ data were 225.3 $\mu$g and 169.1 $\mu$M, respectively.

As described above, in the in vitro rheumatoid model (DSEK cells), the growth of the rheumatoid cells was inhibited in the well to which agarobiose was added as compared with the control well to which PBS was added. Furthermore, it was recognized that the compound not only maintains its growth inhibitory activity but also tends to enhance the activity over time.

These results demonstrate that agarobiose has an antirheumatic activity. Therefore, it is expected that agarobiose would be developed as therapeutic agents and healthy foods useful for chronic rheumatism.

150 $\mu$l of a culture supernatant was collected from a well containing a culture of DSEK cells over time at intervals of 24 hours. The effects of agarobiose on the production (expression) of cytokines (human TGF-$\beta$, human FGF-$\beta$ and human IL-10) from the cell were determined using ELISA kits specific for the respective cytokines (from Intergen for human FGF-$\beta$ and human IL-10; and from Promega for human TGF-$\beta$).

As a result, agarobiose exhibited activities of inhibiting the production of human IL-10, human FGF-$\beta$ and human TGF-$\beta$.

Example 13

HL-60 cells (ATCC CCL-240) were suspended in RPMI 1640 medium (Bio Whittaker, 12-702F) containing 10% fetal calf serum (Gibco) and 100 $\mu$g hydroxyurea at a concentration of 5×10$^5$ cells/ml. 20 ml of the suspension was added to a 10-cm Petri dish. The dish was incubated at 37° C. overnight in the presence of 5% $CO_2$ to make the cells arrest at G1 phase. The cells were collected by centrifugation and resuspended in RPMI 1640 medium containing 10% fetal calf serum (Gibco) and 100 $\mu$M hydroxyurea at a concentration of 5×10$^5$ cells/ml. 5 ml of the suspension was added to each well of a 6-well microtiter plate. On the other hand, as cells without the treatment with hydroxyurea, HL-60 cells were suspended in RPMI 1640 medium containing 10% fetal calf serum (Gibco) at a concentration of 1×10$^5$ cells/ml. 5 ml of the suspension was added to each well of a 6-well microtiter plate. 50 $\mu$l of a solution containing agarobiose at a concentration of 80, 60, 40 or 20 mM in water, or 50 $\mu$l of a solution containing the agarohexaose at a concentration of 80, 60, 40 or 20 mM in water was added to the well containing the cells treated with hydroxyurea. 50 $\mu$l of a solution containing agarobiose at a concentration of 40, 30, 20 or 10 mM in water, or 50 $\mu$l of a solution containing agarohexaose at a concentration of 40, 30, 20 or 10 mM in water was added to the well containing the cells without the treatment with hydroxyurea. The plate was incubated for additional 48 hours. Cells collected by centrifuging the culture were suspended in 5 ml of fresh RPMI 1640 medium containing 10% fetal calf serum (Gibco). 100 $\mu$l of the suspension was used for measuring the viable cell number using Premix WST-1 Cell Proliferation Assay System (Takara Shuzo, MK400).

For each of the samples, the concentration at which 50% of the proliferation is inhibited ($IC_{50}$) for the cells treated with hydroxyurea was higher than that for the cells without the treatment with hydroxyurea. The results are shown in Table 8. Table 8 summarizes $IC_{50}$ ($\mu$M) for each of the samples. These results demonstrate that agarooligosaccharides are less toxic to cells arrested at G1 phase. It is considered that agarooligosaccharides are agents less toxic to a living body because most of cells in a living body are arrested at G1 phase.

TABLE 8

| | Cells treated with hydroxyurea ($\mu$M) | Cells without treatment with hydroxyurea ($\mu$M) |
|---|---|---|
| Agarobiose | 401 | 210.6 |
| Agarohexaose | 383 | 205.3 |

Example 14

(1) RAW264.7 cells (ATCC TIB 71) were suspended in Dulbecco's modified Eagle's medium (Bio Whittaker, 12-604F) containing 10% fetal calf serum (Gibco) at a concentration of 3×10$^5$ cells/ml. 5 ml of the suspension was added to each well of a 6-well microtiter plate and the plate was incubated at 37° C. overnight in the presence of 5% $CO_2$. 50 $\mu$l of a solution containing agarobiose or agarohexaose at a concentration of 10 mM in water was added to the well. The plate was incubated for 0 or 6 hours. 50 $\mu$l of a solution containing lipopolysaccharide (LPS, Sigma, L-2012) at a concentration of 100 $\mu$g/ml in water was added to the well. The plate was incubated for additional 12 hours. The cells were recovered by detaching the cells from the plate using a scraper and suspended in phosphate buffered saline containing 1 $\mu$g/ml pepstatin A (Sigma, P5318), 1 $\mu$g/ml leupeptin (Sigma, L2884), 1 mM phenylmethylsulfonyl fluoride (Nacalai Tesque, 273-27), 10 mM ethylenediaminetetraacetic acid disodium salt and 0.1% Triton X-100. A supernatant obtained by centrifuging the suspension after freezing and thawing was used as a protein fraction. The content of protein in the protein fraction was determined using Micro BCA Protein Assay Reagent (a product of Pierce sold by Takara Shuzo, P7411). A sample from the protein fraction prepared as described above was mixed with an equal volume of 0.125 M tris-hydrochloride buffer (pH 6.8) containing 4% sodium lauryl sulfate (SDS), 2% 2-mercaptoethanol, 0.001% Bromophenol Blue and 20% glycerol. After treatment at 100° C. for 5 minutes, the mixture was loaded on 7.5% SDS-polyacrylamide gel and electrophoresed at a constant current of 20 mA. After electrophoresis, the gel was transferred to a PVDF membrane (Millipore, IPVH000 10) at a constant voltage of 15 V for 25 minutes using a blotting buffer (containing 48 mM tris, 39 mM glycine, 20% methanol and 0.0375% SDS) and Trans-Blot SD Cell Semi-Dry blotting apparatus (Bio-Rad) according to the attached protocol. After transferring, the PVDF membrane was blocked in a solution of Block Ace (Dainippon Pharmaceutical, UK-B25) at 4° C. overnight. After blocking, the membrane washed three times in phosphate buffered saline containing 0.1% Tween 20 for 15 minutes with gentle shaking. The membrane was reacted in phosphate buffered saline containing 10% Block Ace, 0.1% Tween 20 and 50 ng/ml of anti-cyclooxygenase 2 antibody (Transduction Laboratories, C22420) at room temperature for 1 hour with gentle shaking, and then washed three times in phosphate buffered saline containing 0.1% Tween 20 for 15 minutes with gentle shaking. The membrane was reacted in phosphate buffered saline containing 10% Block Ace, 0.1% Tween 20 and 0.1% peroxidase-labeled rabbit anti-mouse IgG (H+L) antibody (Zymed, 61-6520) at room temperature for 1 hour with gentle shaking, and then washed five times in phosphate buffered saline containing 0.1% Tween 20 for 15 minutes with gentle shaking. The PVDF membrane was stained using Western Blot Chemiluminescence Reagent Plus (a product of NEN Life Science Products sold by Daiichi Pure Chemicals, NEL103) according to the attached protocol and exposed to an X-ray film (Kodak, CAT165 1454). After exposure, the film was developed using FPM800 (Fuji Film).

As a result, cyclooxygenase 2 protein was detected for the cells to which LPS was added. On the other hand, the increase in cyclooxygenase 2 protein expression induced by LPS was not suppressed in cells to which agarobiose or agarohexaose was added 0 or 6 hours before the addition of LPS.

(2) RAW264.7 cells (ATCC TIB 71) were suspended in Dulbecco's modified Eagle's medium (Bio Whittaker, 12-604F) containing 10% fetal calf serum (Gibco) at a concentration of $3\times10^5$ cells/ml. 5 ml of the suspension was added to each well of a 6-well microtiter plate and the plate was incubated at 37° C. overnight in the presence of 5% $CO_2$. 50 µl of a solution containing agarobiose or agarohexaose at a concentration of 10 mM in water was added to the well. The plate was incubated for 0 or 6 hours. 50 µl of a solution containing lipopolysaccharide (LPS, Sigma, L-2012) at a concentration of 100 µg/ml in water was added to the well. The plate was incubated for additional 5 hours. The culture supernatant was removed, and 1 ml of a solution of Catrimox-14 (a product of Iowa Biotechnology sold by Takara Shuzo, WA002) was added to the well. After pipetting, the solution was collected. An RNA was prepared according to the attached protocol. The RNA prepared as described above was subjected to RT-PCR using RNA-PCR Kit (AMV) Ver. 2.1 (Takara Shuzo, R019A). A reverse transcription reaction was conducted using a random primer (N6) (Takara Shuzo, 3801) at 30° C. for 10 minutes, at 42° C. for 30 minutes and 99° C. for 5 minutes. PCR was carried out using the synthesized cDNA as a template and primers for cyclooxygenase 2 (GGCACTTGCATTGATGGTGGCT: SEQ ID NO:1 and CAAGCAGTGGCAAGGCCTCCA: SEQ ID NO:2) as follows: 94° C. for 2 minutes; 30 cycles of 94° C. for 30 seconds, 55° C. for 1 minute and 72° C. for 1 minute; 72° C. for 5 minutes. After reaction, the samples were loaded onto 2% agarose gel and electrophoresed at 100 V. After electrophoresis, the gel was stained with ethidium bromide and observed under UV irradiation.

As a result, a band for the cyclooxygenase 2 mRNA was detected for the cells to which LPS was added. On the other hand, the increase in the cyclooxygenase 2 mRNA synthesis induced by LPS was not suppressed in cells to which agarobiose or agarohexaose was added 0 or 6 hours before the addition of LPS.

Based on the results described in Example 14 as well as those described in Example 15 below, it is considered that the inhibition of prostaglandin $E_2$ production by agarooligosaccharides is not inhibition of cyclooxygenase 2 expression.

Example 15

(1) RAW264.7 cells (ATCC TIB 71) were suspended in Dulbecco's modified Eagle's medium (Bio Whittaker, 12-604F) containing 10% fetal calf serum (Gibco) at a concentration of $1\times10^6$ cells/ml. 20 ml of the suspension was added to a 10-cm Petri dish and the dish was incubated at 37° C. overnight in the presence of 5% $CO_2$. 200 µl of a solution containing agarohexaose or DGE (obtained in Example 15-(2) below) at a concentration of 10 mM in water was added to the dish. The dish was incubated for 5 hours. 200 µl of a solution containing lipopolysaccharide (LPS, Sigma, L-2012) at a concentration of 100 µg/ml in water was added thereto. The dish was incubated for additional 12 hours. As a control, 200 µL of water was added in place of the sample. The cells were recovered by detaching the cells from the plate using a scraper and suspended in 0.1 M tris buffer (pH 8.0) containing 1 µg/ml pepstatin A (Sigma, P5318), 1 µg/ml leupeptin (Sigma, L2884) and 1 mM phenylmethylsulfonyl fluoride (Nacalai Tesque, 273-27). The cell membrane was destroyed by sonication. A supernatant collected by centrifugation was used as a crude enzyme fraction. The content of protein in the crude enzyme fraction was determined using Micro BCA Protein Assay Reagent (a product of Pierce sold by Takara Shuzo, P7411). 2.5 µL of 200 mM aqueous solution of glutathione (Nacalai Tesque, 170-50), 2.5 µL of a suspension containing L-adrenaline (Nacalai Tesque, 010-04) at a concentration of 200 mM in water, and 1 µL of 3 mM solution of arachidonic acid (Cayman, 90010.1) or 1 µL of 100 µg/mL solution of prostaglandin $H_2$ (Cayman, 17020) were added to 100 µL of the sample from the crude enzyme fraction prepared as described above. The mixture was reacted at 37° C. for 30 minutes. The reaction was stopped by heating at 100° C. for 2 minutes. The content of prostaglandin $E_2$ in the reaction mixture was measured using Prostaglandin $E_2$ ELISA Kit (Neogen, 404110).

Figure 13:
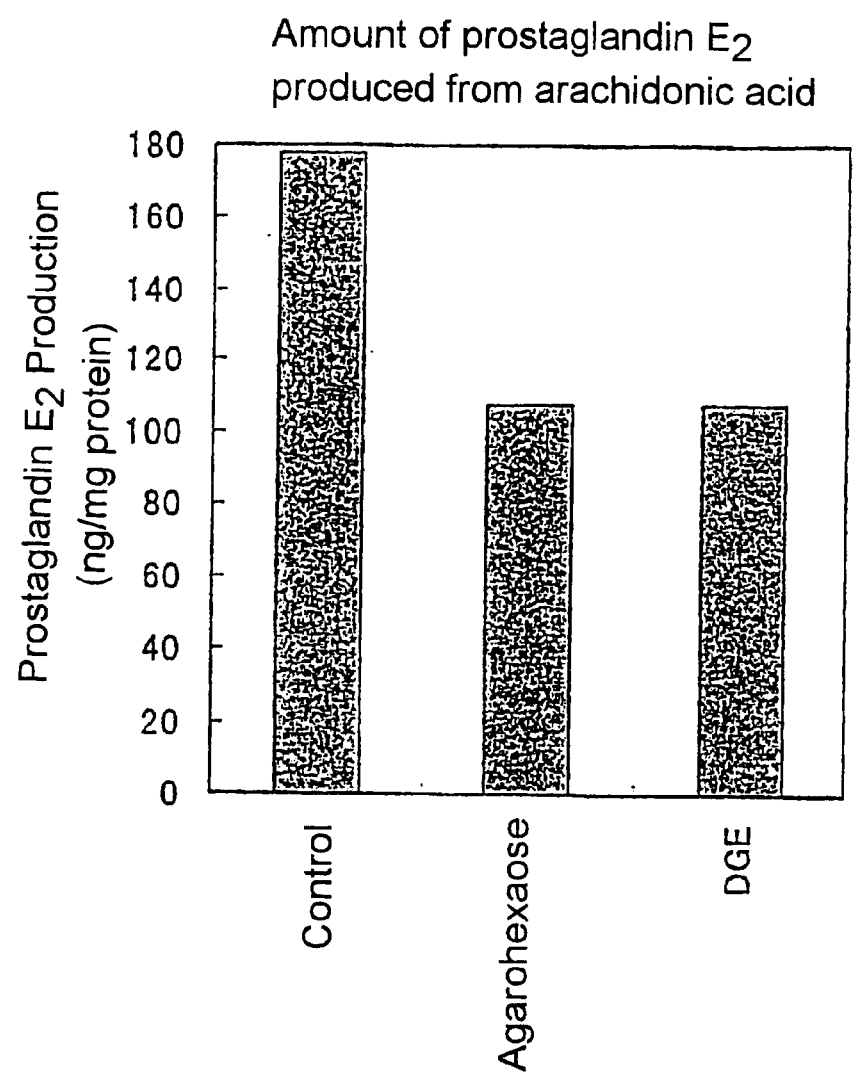
FIG. 13 illustrates the generation of prostaglandin $E_2$ when arachidonic acid was added to each sample.
Figure 14:
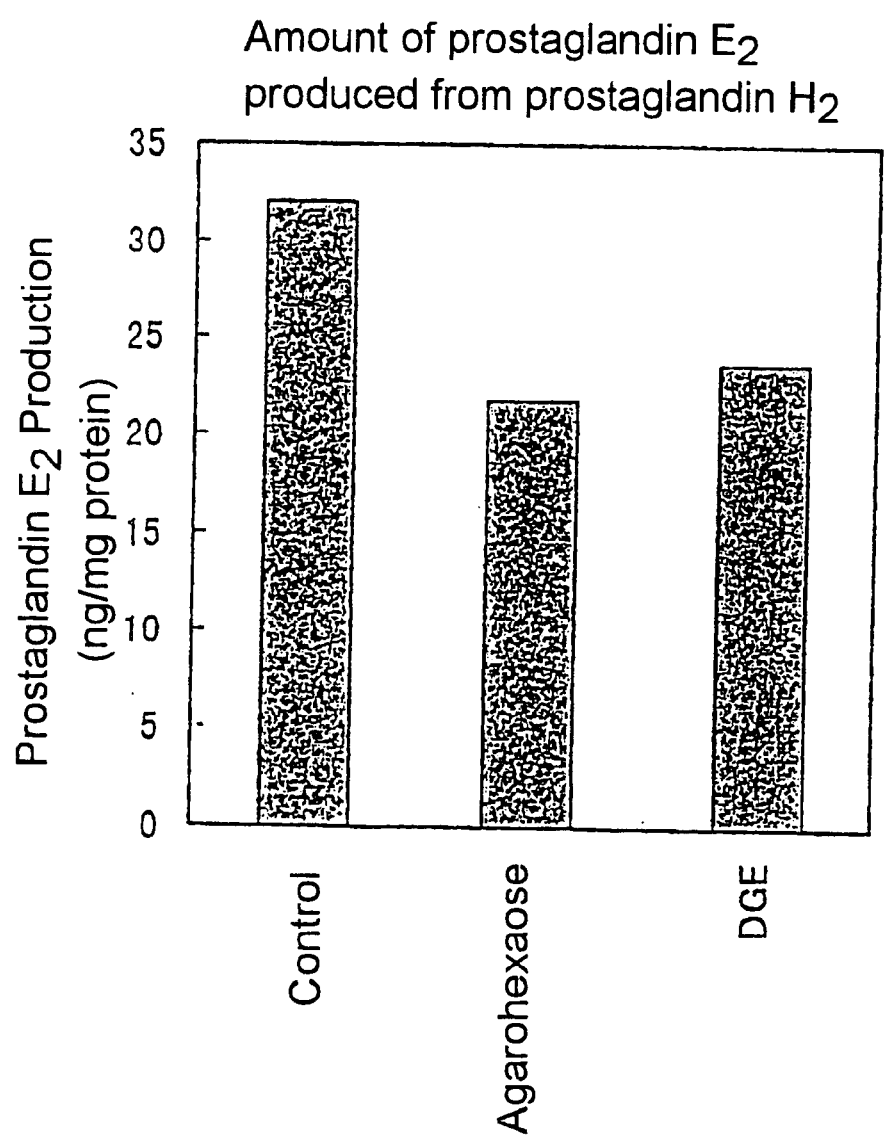
FIG. 14 illustrates the generation of prostaglandin $E_2$ when prostaglandin $H_2$ was added to each sample.

As a result, the production of prostaglandin $E_2$ in the cells to which agarohexaose or DGE was added was suppressed as compared with the control when either arachidonic acid or prostaglandin $H_2$ was added. It is considered that these results suggest a mode of action in which agarohexaose or DGE inhibits the prostaglandin $E_2$ downstream of the prostaglandin $H_2$ production process. FIG. 13 illustrates the generation of prostaglandin $E_2$ when arachidonic acid was added to each sample. The horizontal axis represents the respective samples and the vertical axis represents the amount of produced prostaglandin $E_2$ (ng/ml) per mg protein. FIG. 14 illustrates the generation of prostaglandin $E_2$ when prostaglandin $H_2$ was added to each sample. The horizontal axis represents the respective samples and the vertical axis represents the amount of produced prostaglandin $E_2$ (ng/ml) per mg protein.

(2) DGE (L-glycero-1,5-epoxy-1α,β, 6-dihydroxy-cis-hex-3-en-2-one) of formula X:

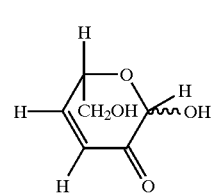

(X)

was prepared.

2.5 g of commercially available agar (Agar Noble) was suspended in 50 ml of 0.1 N HCl and the suspension was heated at 100° C. for 13 minutes to prepare a solution. After cooling to room temperature, the pH was adjusted to 12 using NaOH, and the solution was then neutralized.

The neutralized solution was separated on normal phase HPLC as follows. The fraction at retention time of 4.05 to 4.16 minutes was prepared in large quantities to obtain DGE.

Column: PALPAK Type S (4.6×250 mm, Takara Shuzo);
Mobile Phase A: 90% aqueous acetonitrile solution;
Mobile Phase B: 50% aqueous acetonitrile solution;
Flow rate: 1 ml/min.;
Elution: Mobile Phase A (10 min.)→linear gradient from Mobile Phase A to Mobile Phase B (40 min.)→Mobile Phase B (10 min.);
Detection: absorbance at 195 nm;
Column temperature: 40° C.

Example 16

2.5 μL of 200 mM aqueous solution of glutathione, 2.5 μL of a suspension containing L-adrenaline at a concentration of 200 mM in water, and 1 μL of 100 mM aqueous solution of agarobiose, 100 mM aqueous solution of agarohexaose or 10 mM aqueous solution of DGE as a sample were added to 100 μL of the control sample from the crude enzyme fraction prepared in Example 15. 1 μL of water was added as a negative control. 1 μL of 13 mM nimesulide (Cayman, 70640) solution was added as a positive control. 1 μL of 3 mM arachidonic acid solution was then added to start the reaction. The mixture was reacted at 37° C. for 5 minutes. The reaction was stopped by heating at 100° C. for 2 minutes. The content of prostaglandin $E_2$ in the reaction mixture was measured using Prostaglandin $E_2$ ELISA Kit.

Figure 15:
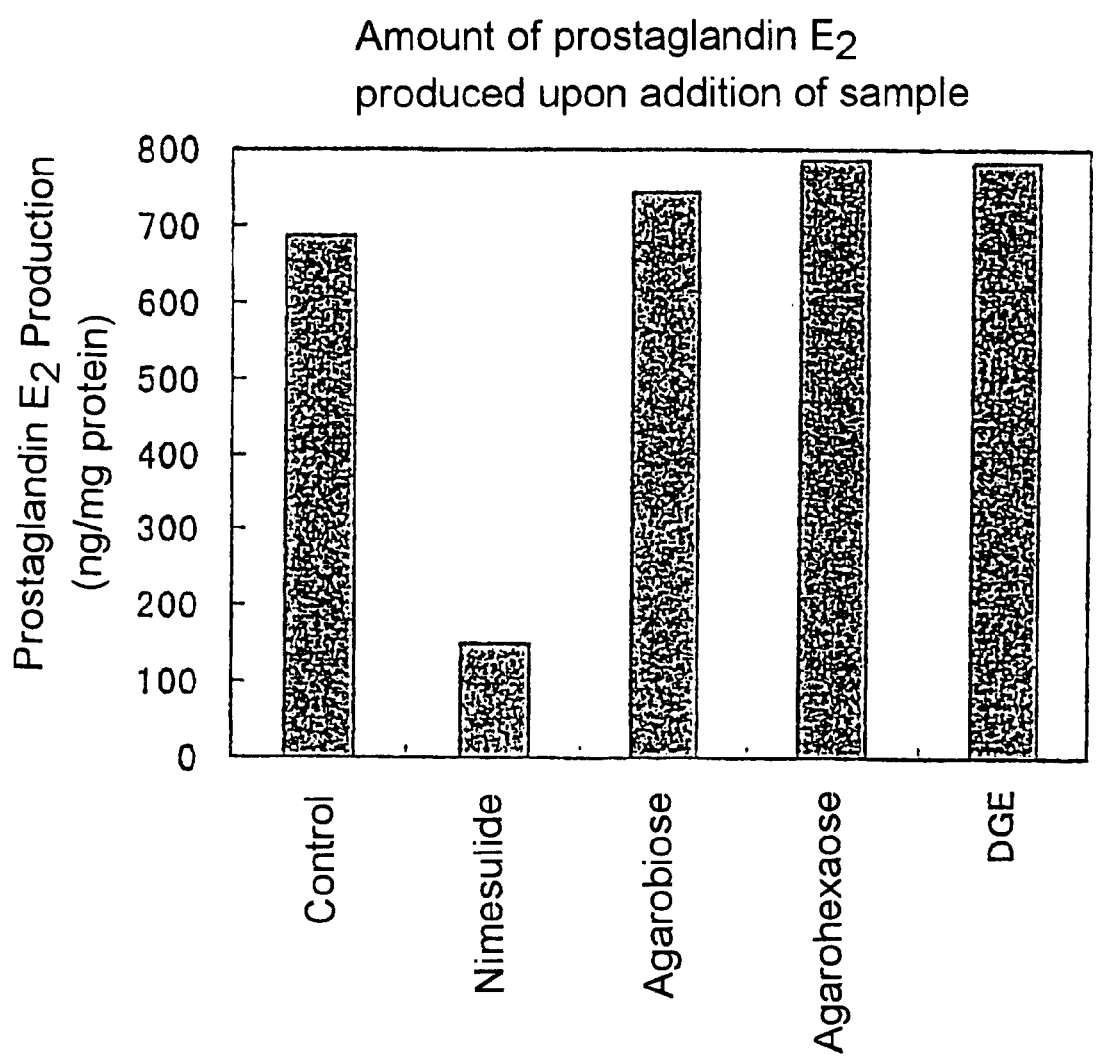
FIG. 15 illustrates the generation of prostaglandin $E_2$ when each sample was added.

As a result, the production of prostaglandin $E_2$ in the cells to which nimesulide was added was suppressed. However, prostaglandin $E_2$ production in cells to which either agarobiose, agarohexaose or DGE was added was not suppressed. Thus, it is considered that agarobiose, agarohexaose and DGE inhibit none of the enzymes involved in the synthesis of prostaglandin $E_2$ from arachidonic acid. The results are shown in FIG. 15. FIG. 15 illustrates the generation of prostaglandin $E_2$ when each sample was added. The horizontal axis represents the respective samples and the vertical axis represents the amount of produced prostaglandin $E_2$ (ng/ml) per mg protein.

Example 17

4 ml of RPMI 1640 medium (Bio Whittaker, 12-702F) containing 10% fetal calf serum was intraperitoneally injected into ddy mouse (Japan SLC, female, 7 weeks old) The medium was removed after extensive massage to obtain celiac cells. The celiac cells were suspended in RPMI 1640 medium containing 10% fetal calf serum at a concentration of $10^6$ cells/ml. 500 μl of the suspension was added to each well of a 48-well microtiter plate and the plate was incubated at 37° C. for 2 hours in the presence of 5% $CO_2$. Adhesive cells obtained by removing the culture supernatant were used as celiac macrophaaes. 500 μl of fresh Dulbecco's modified Eagle's medium (Bio Whittaker, 12-917F) without Phenol Red containing 10% fetal calf serum and 2 mM L-glutamine was added to each well. 5 μl of 20, 10 or 5 mM aqueous solution of agarobiose obtained in Referential Example 1 and 5 μl of 10 μg/ml aqueous solution of 12-O-tetradecanoylphorbol 13-acetate (TPA, Gibco, 13139-019) were added to the well. The plate was incubated for additional 14 hours, and the culture supernatant was then collected. The content of interleukin 6 (IL-6) in the culture supernatant was measured using enzyme immuno sandwich assay (ELISA; Matched antibody Pair Sample Pak-mouse IL6, Endogen). As a control, a group to which the agarobiose aqueous solution or the TPA aqueous solution was not added was provided. All of the measurements were carried out in duplicate.

Figure 16:
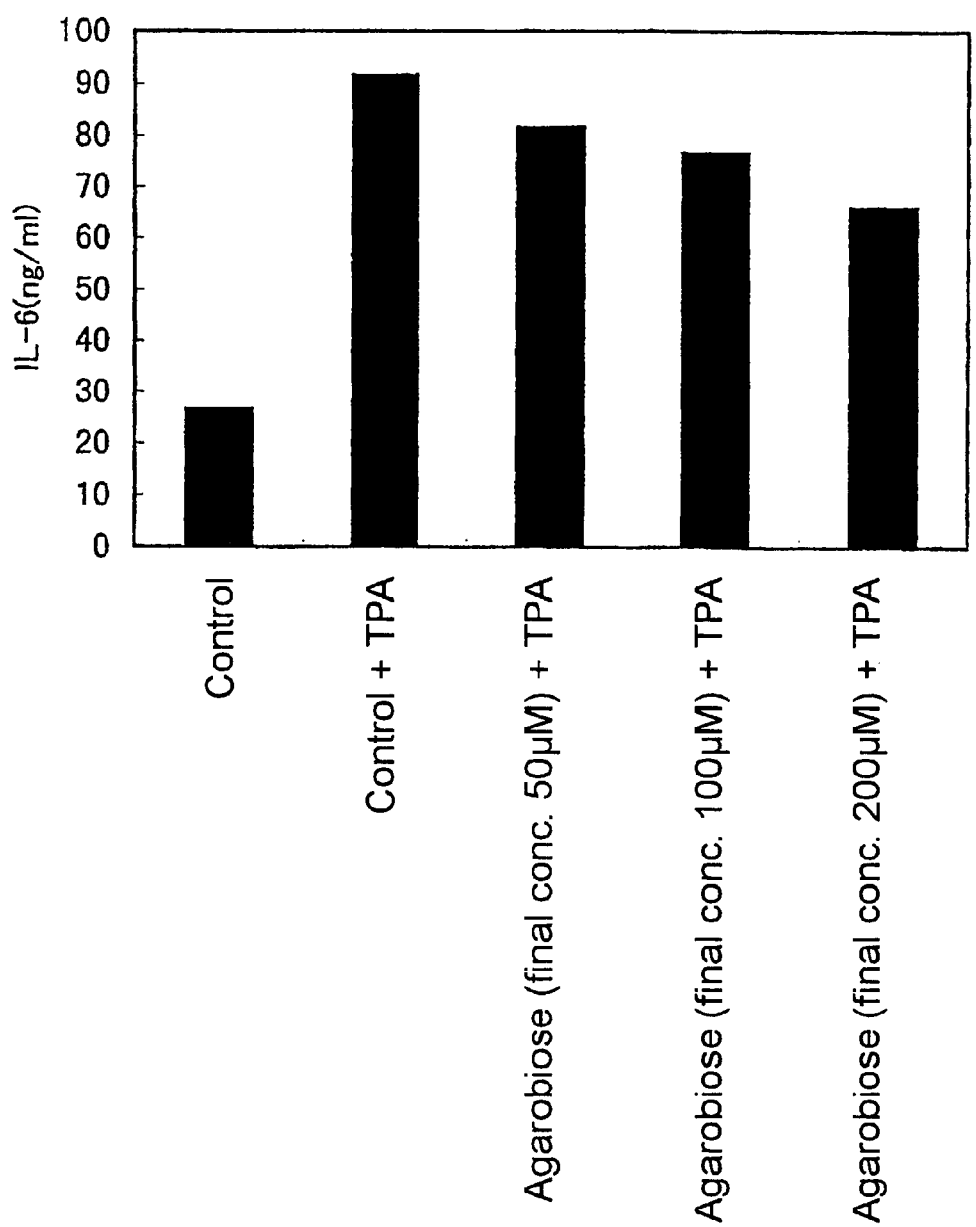
FIG. 16 illustrates the IL-6 concentration in a culture supernatant obtained by culturing under various culture conditions.

As a result, suppression of TPA-induced IL-6 production was observed for the cells to which agarobiose was added in a manner dependent on the concentration of agarobiose. The results are shown in FIG. 16. FIG. 16 illustrates the IL-6 concentration in a culture supernatant obtained by culturing under various culture conditions. The horizontal axis represents the culture conditions, and the vertical axis represents the IL-6 concentration (ng/ml)

Example 18

Agarobiose in Referential Example 3 was dissolved in Tap water at a concentration of 1 or 3% to prepare a 1 or 3% agarobiose solution.

The 1 or 3% agarobiose solution prepared as described above was freely given to ddy mouse (Japan SLC; female, 7 weeks old) as drinking water for 14 days. Tap water was freely given as a control. Each group consisted of 2 mice. 4 ml of RPMI 1640 medium (Bio Whittaker, 12-702F) containing 10% fetal calf serum was intraperitoneally injected. Media removed from 2 mice after extensive massage were combined to obtain celiac cells. The celiac cells were suspended in RPMI 1640 medium containing 10% fetal calf serum at a concentration of $10^6$ cells/ml. 500 μl of the suspension was added to each well of a 48-well microtiter plate and the plate was incubated at 37° C. for 2 hours in the presence of 5% $CO_2$. Adhesive cells obtained by removing the culture supernatant were used as celiac macrophages. 500 μl of fresh Dulbecco's modified Eagle's medium (Bio Whittaker, 12-917F) without Phenol Red containing 10% fetal calf serum and 2 mM L-glutamine, and 5 μl of 100 μg/ml aqueous solution of lipopolysaccharide (LPS, Sigma, L-2012) were added to each well. The plate was incubated for additional 15 hours, and the culture supernatant was then collected. The content of interleukin 6 (IL-6) in the culture supernatant was measured using enzyme immuno sandwich assay. As a control, a group to which LPS was not added was provided. All of the measurements were carried out in duplicate.

Figure 17:
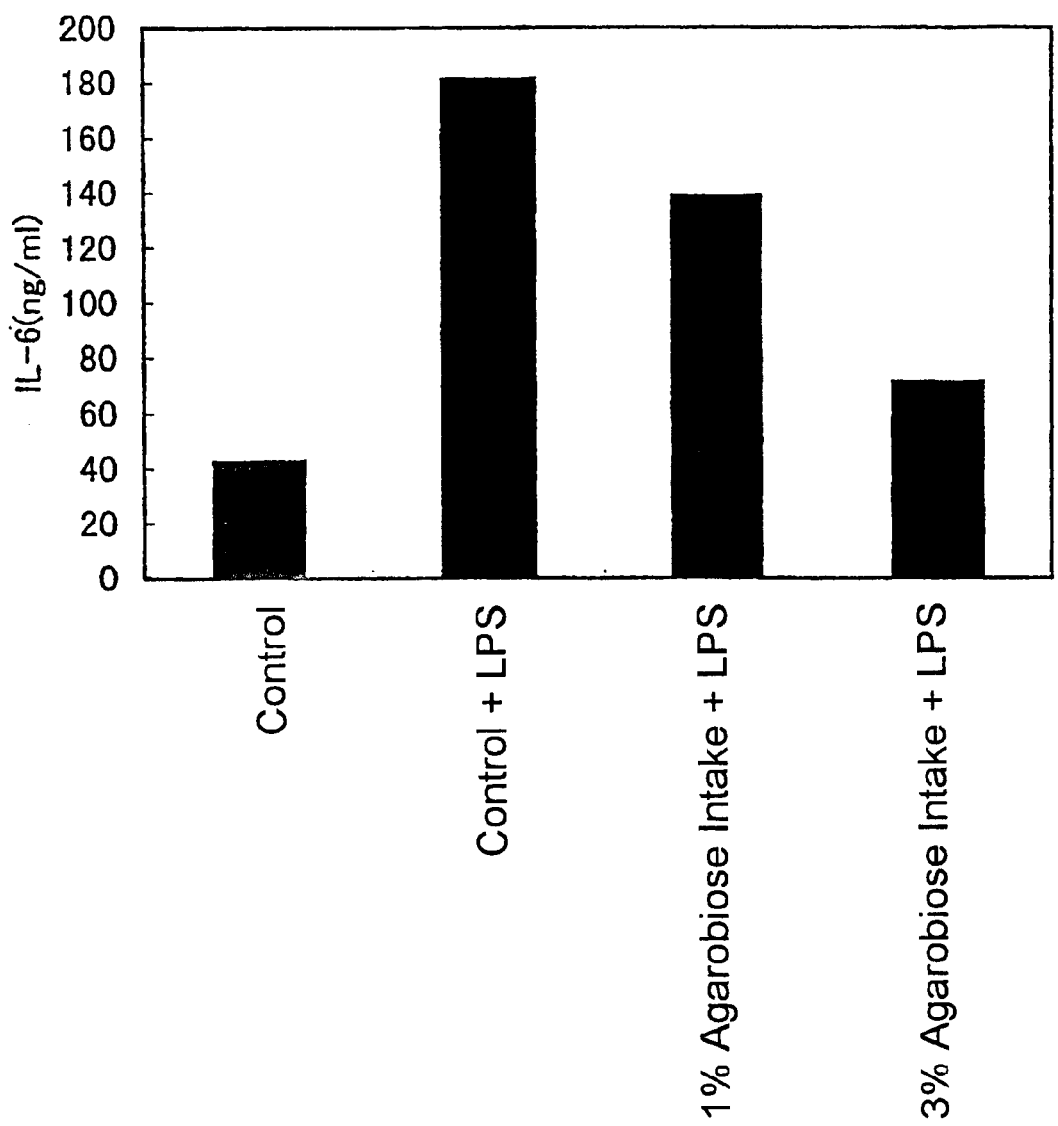
FIG. 17 illustrates the IL-6 concentration in a culture supernatant obtained by culturing under various culture conditions.

As a result, suppression of LPS-induced IL-6 production was observed for the celiac macrophages prepared from the mouse to which the agarobiose solution was freely given as drinking water in a manner dependent on the concentration of agarobiose. The results are shown in FIG. 17. FIG. 17 illustrates the IL-6 concentration in a culture supernatant obtained by culturing under various culture conditions. The horizontal axis represents the conditions, and the vertical axis represents the IL-6 concentration (ng/ml).

RAW264.7 cells (ATCC TIB 71) were suspended in Dulbecco's modified Eagle's medium (Bio Whittaker, 12-604F) containing 10% fetal calf serum (Gibco) at a concentration of $3×10^5$ cells/ml. 0.5 ml of the suspension was added to each well of a 48-well microtiter plate and the plate was incubated at 37° C. overnight in the presence of 5% $CO_2$. 5 μl of a solution containing agarobiose or agarohexaose in Referential Example 1 at a concentration of 10 mM in water was added to the well. After incubation for additional 5 hours, 5 μl of a solution of lipopolysaccharide (LPS, Sigma, L-2012) at a concentration of 100 μg/ml in water was added the well. After incubation for 18 hours, a culture supernatant was collected. The content of interleukin 10 (IL-10) in the culture supernatant was measured using enzyme immuno sandwich assay. As a control, a group to which the sample or the LPS aqueous solution was not added was provided. All of the measurements were carried out in duplicate.

Figure 18:
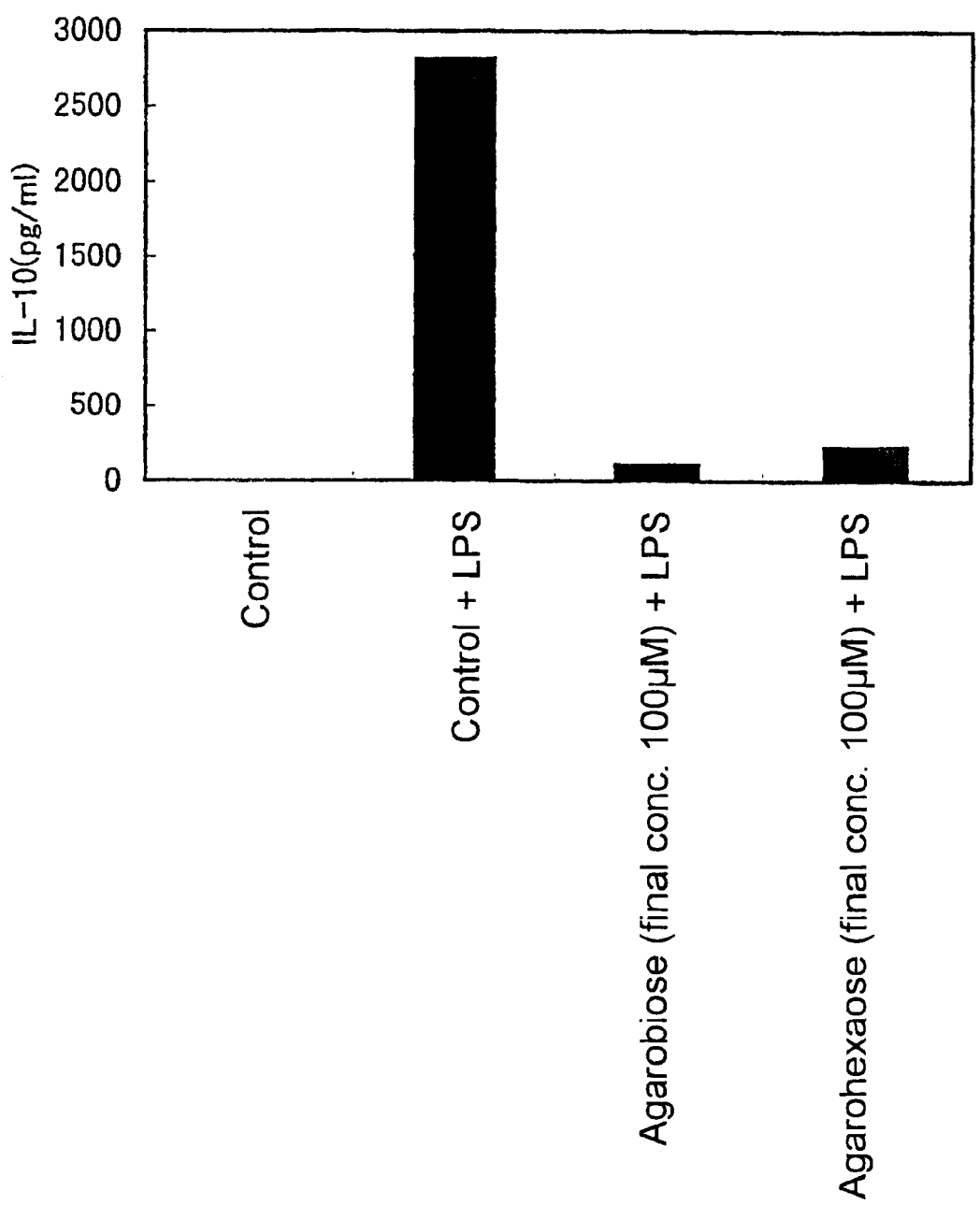
FIG. 18 illustrates the IL-10 concentration in a culture supernatant obtained by culturing under various culture conditions.

As a result, inhibition of LPS-induced IL-10 production was observed for cells to which agarobiose or agarohexaose was added. The results are shown in FIG. 18. FIG. 18 illustrates the IL-10 concentrations in culture supernatants obtained by culturing under various culture conditions. The horizontal axis represents the culture conditions and the vertical axis represents the IL-10 concentration (pg/ml).

Example 19

RAW264.7 cells (ATCC TIB 71) were suspended in Dulbecco's modified Eagle's medium (Bio Whittaker, 12-604F) containing 10% fetal calf serum (Gibco) at a concentration of $3 \times 10^5$ cells/ml. 5 ml of the suspension was added to each well of a 6-well microtiter plate and the plate was incubated at 37° C. overnight in the presence of 5% $CO_2$. 50 µl of a solution containing agarobiose or agarohexaose in Referential Example 1 at a concentration of 20 mM, 10 mM or 5 mM in water was added to the well. The plate was incubated for 15 hours. A positive control for heme oxygenase 1 induction in which 5 µl of 3 mM solution of 15-deoxy-Δ12,14 prostaglandin $J_2$ (Cayman Chemical, 18570) in dimethyl sulfoxide was added, and a negative control in which water was added were provided. The cells were recovered by detaching the cells from the plate using a scraper and suspended in 0.1 M tris-HCl buffer (pH 7.5) containing 0.05 mM pepstatin A (Sigma, P5318), 0.2 mM leupeptin (Sigma, L2884), 1 mM phenylmethylsulfonyl fluoride (Nacalai Tesque, 273-27), 10 mm ethylenediaminetetraacetic acid disodium salt and 0.1% Triton X-100. A supernatant obtained by centrifuging the suspension after freezing and thawing was used as a protein fraction. The content of protein in the protein fraction was determined using Micro BCA Protein Assay Reagent (a product of Pierce sold by Takara Shuzo, P7411). A sample from the protein fraction prepared as described above was mixed with an equal volume of 0.125 M tris-hydrochloride buffer (pH 6.8) containing 4% sodium lauryl sulfate (SDS), 2% 2-mercaptoethanol, 0.001% Bromophenol Blue and 20% glycerol. After treatment at 100° C. for 5 minutes, a portion corresponding to 10 µg of protein was loaded on 12.5% SDS-polyacrylamide gel and electrophoresed at a constant current of 20 mA. After electrophoresis, the gel was transferred to a PVDF membrane (Millipore, IPVH000 10) at a constant voltage of 15 V for 25 minutes using a blotting buffer (containing 48 mM tris, 39 mM glycine, 20% methanol and 0.0375% SDS) and Trans-Blot SD Cell Semi-Dry blotting apparatus (Bio-Rad) according to the attached protocol. After transferring, the PVDF membrane was blocked in a solution of Block Ace (Dainippon Pharmaceutical, UK-B25) at 4° C. overnight. After blocking, the membrane washed three times in phosphate buffered saline containing 0.1% Tween 20 for 15 minutes with gentle shaking. The membrane was reacted in phosphate buffered saline containing 10% Block Ace, 0.1% Tween 20 and 200 ng/ml of anti-heme oxygenase 1 antibody (N-19; Santa Cruz, sc-7696) at room temperature for 1 hour with gentle shaking, and then washed three times in phosphate buffered saline containing 0.1% Tween 20 for 15 minutes with gentle shaking. The membrane was reacted in phosphate buffered saline containing 10% Block Ace, 0.1% Tween 20 and 0.1% peroxidase-labeled rabbit anti-goat IgG (H+L) antibody (Zymed, 61-1620) at room temperature for 1 hour with gentle shaking, and then washed five times in phosphate buffered saline containing 0.1% Tween 20 for 15 minutes with gentle shaking. The PVDF membrane was stained using Western Blot Chemiluminescence Reagent Plus (a product of NEN Life Science Products sold by Daiichi Pure Chemicals, NEL103) according to the attached protocol and exposed to an X-ray film (Kodak, CAT165 1454). After exposure, the film was developed using FPM800 (Fuji Film).

As a result, a band for heme oxygenase 1 protein was observed for the cells to which either agarobiose or agarohexaose was added. The intensity of the band depended on the concentration of agarobiose or agarohexaose. The results are shown in Table 9. In the table, the intensity of the band for heme oxygenase 1 protein is expressed by the mark+. Specifically, – represents no band observed, and increase in the intensity of the band is represented as follows:+–<+<++.

TABLE 9

| Sample | Intensity of band for heme oxygenase 1 protein |
|---|---|
| Water (negative control) | – |
| Agarobiose at final concentration of 200 µM | ++ |
| Agarobiose at final concentration of 100 µM | + |
| Agarobiose at final concentration of 50 µM | +– |
| Agarohexaose at final concentration of 200 µM | ++ |
| Agarohexaose at final concentration of 100 µM | + |
| Agarohexaose at final concentration of 50 µM | +– |
| 15-deoxy-Δ12,14 prostaglandin $J_2$ (positive control) | + |

INDUSTRIAL APPLICABILITY

The present invention provides a pharmaceutical composition, a functional food and a functional drink which are useful for maintaining homeostasis in a living body and for treating or preventing diseases such as diabetes, rheumatism and age-related diseases. The compound used in the present invention exhibits a remarkable activity of inhibiting carcinogenesis. Thus, it is also useful as an additive for a food for inhibiting carcinogenesis.

Sequence Listing Free Text

SEQ ID NO:1: Designed oligonucleotide primer to amplify cyclooxygenase 2 mRNA.

SEQ ID NO:2: Designed oligonucleotide primer to amplify cyclooxygenase 2 mRNA.

What is claimed is:

1. A pharmaceutical composition which contains as an active ingredient at least one member selected from the group consisting of:

a compound selected from the group consisting of 3,6-anhydrogalactopyranose of formula I:

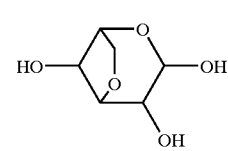

(I)

an aldehyde and a hydrate thereof, and 2-O-methylated derivatives and 2-O-sulfated derivatives of the 3,6-anhydrogalactopyranose, the aldehyde and the hydrate; and a soluble saccharide that contains said compound at its reducing end, said pharmaceutical composition being used for treating diabetes, rheumatism, a disease that requires inhibition of inflammation for its treatment, a disease that requires inhibition of α-glycosidase for its treatment, a disease that requires inhibition of prostaglandin synthesis for its treatment, a disease that requires inhibition of endotoxin shock for its treatment, a disease that requires inhibition of interleukin production for its treatment, a disease that requires induction of heme oxygenase production for its treatment or prevention, a disease that requires inhibition of tumor necrosis factor production for its treatment, or a disease that requires inhibition of carcinogenesis for its treatment.

2. The pharmaceutical composition according to claim 1, wherein the saccharide is a product produced by acid decomposition under acidic conditions below pH 7 of a substance containing at least one compound selected from the group consisting of 3,6-anhydrogalactopyranose of formula I, an aldehyde and a hydrate thereof, and 2-O-methylated derivatives and 2-O-sulfated derivatives of the 3,6-anhydrogalactopyranose, the aldehyde and the hydrate.

3. The pharmaceutical composition according to claim 2, wherein the substance containing at least one compound selected from the group consisting of 3,6-anhydrogalactopyranose of formula I, an aldehyde and a hydrate thereof, and 2-O-methylated derivatives and 2-O-sulfated derivatives of the 3,6-anhydrogalactopyranose, the aldehyde and the hydrate is at least one substance selected from the group consisting of agar, agarose and carrageenan.

4. The pharmaceutical composition according to any one of claims 1 to 3, wherein the saccharide is at least one saccharide selected from the group consisting of agarobiose, agarotetraose, agarohexaose, agarooctaose, κ-carabiose and β-D-galactopyranosyl-3,6-anhydro-2-o-methyl-L-galactose.

5. A food or a drink which contains, which is produced by adding thereto, or which is produced by diluting at least one member selected from the group consisting of:

a compound selected from the group consisting of 3,6-anhydrogalactopyranose of formula I

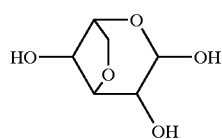

(I)

an aldehyde and a hydrate thereof, and 2-O-methylated derivatives and 2-O-sulfated derivatives of the 3,6-anhydrogalactopyranose, the aldehyde and the hydrate; and a soluble saccharide that contains said compound at its reducing end, said food or drink being adapted for ameliorating the disease states of diabetes, rheumatism, a disease that requires inhibition of α-glycosidase for its treatment, a disease that requires inhibition of prostaglandin synthesis for its treatment, a disease that requires inhibition of endotoxin shock for its treatment, a disease that requires inhibition of interleukin production for its treatment, a disease that requires induction of heme oxygenase production for its treatment, a disease that requires inhibition of tumor necrosis factor production for its treatment, or a disease that requires inhibition of carcinogenesis for its treatment.

6. In a method of formulating a pharmaceutical composition comprising mixing together at least two compounds, the improvement wherein said two compounds are (1) a compound selected from the group consisting of 3,6-anhydrogalactopyranose of formula I,

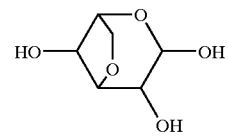

(I)

an aldehyde and a hydrate thereof, and 2-O-methylated derivatives and 2-O-sulfated derivatives of the 3,6-anhydrogalactopyranose, the aldehyde and the hydrate; and (2) a soluble saccharide that contains said compound (1), and wherein said compounds are mixed in proportions suitable to provide an antidiabetic composition, an antirheumatic composition, an anti-inflammatory composition, a composition for inhibiting α-glycosidase, a composition for inhibiting prostaglandin synthesis, a composition for inhibiting endotoxin shock, a composition for inhibiting interleukin production, a composition for inducing heme oxygenase production, a composition for inhibiting tumor necrosis factor production or a composition for inhibiting carcinogenesis.

7. In a method for providing in a patient in need thereof at least one of an antidiabetic effect, an anti-rheumatic effect, an anti-inflammatory effect, an anti-α-glycosidase effect, an anti-prostaglandin synthesis effect, an anti-endotoxin shock effect, an anti-interleukin production effect, an anti-tumor necrosis factor production effect or an anti-carcinogenesis effect, or for inducing heme oxygenase production, comprising administering to said patient an amount effective for such an effect of a pharmaceutical composition, the improvement wherein said pharmaceutical composition comprises a compound selected from the group consisting of 3,6-anhydrogalactopyranose of formula I,

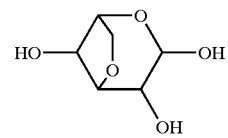

(I)

an aldehyde and a hydrate thereof, and 2-O-methylated derivatives and 2-O-sulfated derivatives of the 3,6-anhydrogalactopyranose, the aldehyde and the hydrate; and a soluble saccharide that contains said compound.

8. The pharmaceutical composition according to claim 1, wherein the saccharide is a product produced by enzymatic digestion of a substance containing at least one compound selected from the group consisting of 3,6-anhydrogalactopyranose of formula I, an aldehyde and a hydrate thereof, and 2-O-methylated derivatives and 2-O-sulfated derivatives of the 3,6-anhydrogalactopyranose, the aldehyde, and the hydrate.

9. The pharmaceutical composition according to claim 8, wherein the substance containing at least one compound selected from the group consisting of 3,6-anhydrogalactopyranose of formula I, an aldehyde and a hydrate thereof, and 2-O-methylated derivatives and 2-O-sulfated derivatives of the 3,6-anhydrogalactopyranose, the aldehyde, and the hydrate is at least one substance selected from the group consisting of agar, agarose and carrageenan.

* * * * *